(12) United States Patent
Lyerly et al.

(10) Patent No.: US 10,842,855 B2
(45) Date of Patent: Nov. 24, 2020

(54) VACCINES AGAINST AN ONCOGENIC ISOFORM OF ESR1 AND METHODS OF USING THE SAME

(71) Applicant: Duke University, Durham, NC (US)

(72) Inventors: Herbert K. Lyerly, Durham, NC (US); Takuya Osada, Durham, NC (US); Zachary C. Hartman, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 16/044,269

(22) Filed: Jul. 24, 2018

(65) Prior Publication Data

US 2018/0326030 A1    Nov. 15, 2018

Related U.S. Application Data

(62) Division of application No. 15/324,183, filed as application No. PCT/US2015/039367 on Jul. 7, 2015, now abandoned.

(60) Provisional application No. 62/021,586, filed on Jul. 7, 2014.

(51) Int. Cl.
| | | |
|---|---|---|
| A61K 39/00 | (2006.01) | |
| A61K 38/17 | (2006.01) | |
| A61P 35/00 | (2006.01) | |
| A61K 38/45 | (2006.01) | |
| A61K 39/395 | (2006.01) | |
| A61K 45/06 | (2006.01) | |
| C07K 16/28 | (2006.01) | |
| C12N 7/00 | (2006.01) | |

(52) U.S. Cl.
CPC .......... *A61K 39/0011* (2013.01); *A61K 38/17* (2013.01); *A61K 38/177* (2013.01); *A61K 38/45* (2013.01); *A61K 39/001104* (2018.08); *A61K 39/001106* (2018.08); *A61K 39/3955* (2013.01); *A61K 45/06* (2013.01); *A61P 35/00* (2018.01); *C07K 16/2818* (2013.01); *C12N 7/00* (2013.01); *C12Y 207/10001* (2013.01); *A61K 2039/53* (2013.01); *C07K 2317/76* (2013.01); *C12N 2740/15034* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 6,734,172 B2 | 5/2004 | Scholler et al. | |
| 7,429,650 B2 * | 9/2008 | Fuqua ............ | G01N 33/57415 536/23.1 |
| 8,445,268 B2 | 5/2013 | Lee et al. | |
| 8,846,080 B2 | 9/2014 | Biemans et al. | |
| 9,216,229 B2 | 12/2015 | Brown et al. | |
| 9,226,959 B2 | 1/2016 | Kramps et al. | |
| 9,855,270 B2 * | 1/2018 | Hager ............... | A61K 31/4025 |
| 9,956,276 B2 | 5/2018 | Lyerly et al. | |
| 10,258,676 B2 * | 4/2019 | Zeng ................. | A61K 39/12 |
| 2003/0228606 A1 | 12/2003 | Tatarewicz et al. | |
| 2003/0232350 A1 | 12/2003 | Afar et al. | |
| 2004/0253606 A1 | 12/2004 | Aziz et al. | |
| 2005/0266409 A1 | 12/2005 | Brown et al. | |
| 2008/0057064 A1 | 3/2008 | Zhou | |
| 2009/0214518 A1 | 8/2009 | Buckanovich et al. | |
| 2010/0055093 A1 | 3/2010 | Shepard et al. | |
| 2010/0279399 A1 | 11/2010 | Robins et al. | |
| 2011/0281748 A1 | 11/2011 | Singh et al. | |
| 2012/0014984 A1 | 1/2012 | Shahabi | |
| 2014/0017259 A1 | 1/2014 | Aurisicchio et al. | |
| 2014/0221329 A1 | 8/2014 | Cronin et al. | |
| 2014/0377261 A1 | 12/2014 | Lyerly et al. | |
| 2015/0047065 A1 | 2/2015 | Brack et al. | |
| 2015/0258099 A1 | 9/2015 | Hager et al. | |
| 2018/0092989 A1 | 4/2018 | Lyerly et al. | |
| 2018/0094050 A1 | 4/2018 | Lyerly et al. | |
| 2018/0282736 A1 | 10/2018 | Lyerly et al. | |

FOREIGN PATENT DOCUMENTS

| | | |
|---|---|---|
| WO | WO 2003/080835 | 10/2003 |
| WO | WO 2011/060260 | 5/2011 |
| WO | WO 2011/146568 | 11/2011 |
| WO | WO 2011/154863 | 12/2011 |

(Continued)

OTHER PUBLICATIONS

Mehta et al (The Breast, Feb. 1, 2014, 23:2-9).*
Agus, DB et al. "Targeting ligand-activiated ErbB2 signaling inhibits breast and prostate tumor growth." (2002) 2:127-37.
Amalfitano A, Hauser MA, Hu H, Serra D, Begy CR, Chamberlain JS. Production and characterization of improved adenovirus vectors with the E1, E2b, and E3 genes deleted. J Virol. 1998;72(2):926-33.
Amin, DN et al. "The role of HER3, the unpretentious emmber of the HER family, in cancer biology and cancer therapuetics." (2010) Semin Cell Dev Biol 2010:8.

(Continued)

*Primary Examiner* — Laura B Goddard
(74) *Attorney, Agent, or Firm* — Quarles & Brady LLP

(57) ABSTRACT

Methods of reducing the likelihood of a cancer or precancer developing resistance to a cancer therapeutic or prevention agent are provided herein. The methods include administering the cancer therapeutic or prevention agent and a vaccine comprising a polynucleotide encoding a polypeptide whose expression or activation is correlated with development of resistance of the cancer or precancer to the cancer therapeutic or prevention agent to a subject. The vaccine may include a polynucleotide encoding an ESR1 polypeptide or a truncation, deletion or substitution mutant thereof. Methods of using the vaccine including the polynucleotide encoding the ESR1 polypeptide to treat a cancer or precancer are also provided.

16 Claims, 14 Drawing Sheets

Specification includes a Sequence Listing.

(56) References Cited

FOREIGN PATENT DOCUMENTS

| WO | WO 2012/125864 | 9/2012 |
|----|----------------|--------|
| WO | WO 2013/056178 | 4/2013 |
| WO | WO 2013/110030 | 7/2013 |
| WO | WO 2016/007499 | 1/2016 |
| WO | WO 2016/007504 | 1/2016 |
| WO | WO 2017/120576 | 7/2017 |

OTHER PUBLICATIONS

Arteaga et al.. Treatment of HER2-positive breast cancer: current status and future perspectives. Nature Reviews Clinical Oncology, 9: 16-32, 2012.

Atkins, MB et al. "Phase I evaluation of intravenous recombinant human interleukin 12 in patients with advanced malignancies." (1997) Clin Cancer Res 3:409-17.

Ben-Kasus, T. et al. "Persistent elimination of ErbB-2/HER2-overexpressing tumors using combinations of monoclonal antibodies: relevance of receptor endocytosis." (2009) Proc Natl Acad Sci USA 106:3294-99.

Binder DC, Engels B, Arina A, Yu P, Slauch JM, Fu YX, et al. Antigen-specific bacterial vaccine combined with anti-PD-L1 rescues dysfunctional endogenous T cells to reject long-established cancer. Cancer immunology research. 2013;1(2):123-33.

Blattman, JN et al. "Cancerimmunotherapy: a treatment for the masses." (2004) Science 305:200-5.

Cai Z, Zhang H, Liu J, Berezov A, Murali R, Wang Q, et al. Targeting erbB receptors. Seminars in cell & developmental biology. 2010;21(9):961-6.

Campbell, MR et al. "HER3 comes of age: new insights into its functions and role in signaling, tumor biology, and cancer therapy." Clin cancer Res (2010) 16:1373-83.

Clay, T. et al., "Polyclonal Immune Responses To Antigens Associated With Cancer Signaling Pathways And New Strategies To Enhance Cancer Vaccines" (2011) Immunolo Res 49(0): 235-247.

Drake, CG et al. Mechanisms of immune evasion by tumors. (2006) Adv Immunol 90:51-81.

Dranoff, G. "Cytokines in cancer pathogenesis and cancer therapy." (2004) Nat Rev Cancer 4:11-22.

Ebctcg, et al., "Relevance of breast cancer hormone receptors and other factors to the efficacy of adjuvant tamoxifen: patient-level meta-analysis of randomised trials" (2011) Lancet 378(9793): 771-784.

Eager, R et al. "GM-CSFF gene-transduced tumor vaccines." (2005) Mol Ther. 12:18-27.

Fourcade J, Sun Z, Pagliano O, Chauvin JM, Sander C, Janjic B, et al. PD-1 and Tim-3 regulate the expansion of tumor antigen-specific CD8(+) T cells induced by melanoma vaccines. Cancer Res. 2014;74(4):1045-55.

Friedman, LM et al. "Synergistic down-regulation of receptor tyrosine kinase by combinations of mAbs: implications for cancer immunotherapy." (2005) Proc Natl Acad Sci USA 102:1915-20.

Fu, J. et al., "Preclinical evidence that PD1 blockade cooperates with cancer vaccine TEGVAX to elicit regression of established tumors" (2014) Cancer Res, 74(15): 4042-4052.

Gala K, Chandarlapaty S. Molecular pathways: HER3 targeted therapy. Clin Cancer Res. 2014;20(6):1410-6.

Gallo, P. et al., "Xenogenic Immunization in Mice Using HER2 DNA Delivered by an Adenoviral Vector" (2005) Int. J. Cancer 113(1):67-77.

Genbank NM_000125.3. Homo sapiens estrogen receptor 1 (ESR1), transcript variant 1, mRNA [online]. Oct. 2, 2011 [retrieved Sep. 10, 2015]. Available on the internet: <URL: http://www.ncbi.nlm.nih.gov/nuccore/170295798?sat=14&satkey=11929788>.

Goldman, B et al. "The cancer vaccine roller coaster." (2009) Nat Biotechnol 27:129-39.

Greenspan, N.S. et al., "Defining epitopes: It's not as easy as it seems," (1999) Nature Biotechnology 7:936-937.

Grupp et al., Chimeric antigen receptor-modified T cells for acute lymphoid leukemia. New England J. Med. 368:1509-18, (2013).

Hartman, Z. et al., "An Adenoviral vaccine encoding full-length inactivated human Her2 exhibits potent immunogenicity and enhanced therapeutic efficacy without oncogenicity" (2010) Clin Cancer Res 16(5): 1466-1477.

Hartman, Z. et al., "Ligand-independent TLR signals generated by ectopic overexpression of MyD88 generate local and systemic anti-tumor immunity" (2010) Cancer Res 70(18): 7209-7220.

Hartman, Z. et al., "Growth of triple-negative breast cancer cells relies upon coordinate autocrine expression of the proinflammatory cytokines IL-6 and IL-8" (2013) Cancer Res 73(11): 3470-3480.

Hartman, Z. et al., Increasing vaccine potency through exosome antigen targeting. Vaccine. Nov. 21, 2011;29(50):9361-7.

He, TC et al. "A simplified system for generating recombinant adenoviruses." (1998) Proc Natl Acad Sci USA 95:2509-14.

Hodges, BL et al. "Adenovirus vectors with the 100K gene deleted and their potential for multiple gene therapy applications." (2001) J Virol 75:5913-20.

Holmes, E.H., "PSMA specific antibodies and their diagnostic and therapeutic use," (2001) Exp. Opin. Invest. Drugs 10(3):511-519.

Hsieh AC, Moasser MM. Targeting HER proteins in cancer therapy and the role of the non-target HER3. Br J Cancer. 2007;97(4):453-7.

Ignatiadis, M. & Sotiriou, C. "Luminal breast cancer: from biology to treatment" (2013) Nature Rev Clin Oncol 10, 494-506.

Karyampudi L, Lamichhane P, Scheid AD, Kalli KR, Shreeder B, Krempski JW, et al. Accumulation of memory precursor CD8 T cells in regressing tumors following combination therapy with vaccine and anti-PD-1 antibody. Cancer Res. 2014;74(11):2974-85.

Kennecke, H. et al., "Metastatic behavior of breast cancer subtypes" (2010) J Oncol 28(20): 3271-3277.

Kershaw, M.H. et al., "Gene-engineered T cells as a superior adjuvant therapy for metastatic cancer" (2004) J Immunol 173(3): 2143-2150.

Kol A, Terwisscha van Scheltinga AG, Timmer-Bosscha H, Lamberts LE, Bensch F, de Vries EG, et al. HER3, serious partner in crime: therapeutic approaches and potential biomarkers for effect of HER3-targeting. Pharmacol Ther. 2014;143(1):1-11.

Laheru, Da eta 1. "Genes to vaccines for immunotherapy: how the molecular biology revolution has influenced cancer immunology." (2005) Mol Cancer Ther 4:1645-52.

Lee-Hoeflich, ST et al. "A central role for HER3 in HER2-amplified breast cancer: implications for targeted therapy." (2008) Cancer Res 68:5878-87.

Leonard, JP et al. "Effects of single-dose interleukin-12 exposure on interleukin-12-associated toxicity and interferon-γ production." (1997) Blood 90:2541-8.

Li B, VanRoey M, Wang C, Chen TH, Korman A, Jooss K. Anti-programmed death-1 synergizes with granulocyte macrophage colony-stimulating factor—secreting tumor cell immunotherapy providing therapeutic benefit to mice with established tumors. Clin Cancer Res. 2009;15(5):1623-34.

Luo, et al. "A protocol for rapid generation of recombinant adenoviruses using the AdEasy system" (2007) Nature Protocols 2:1236.

Makhija, S et al. "clinical activity of gemcitabine plus pertuzumab in platinum-resistant ovarian cancer, fallopian tube cancer, or primary peritoneal cancer." (2010) J Clin Oncol 28:1215-23.

Morse, MA et al. Synergism from combined immunologic and pharmacologic inhibition of HER2 in vivo. (2010) Int J Cancer 126:2893-903.

Nabholtz, J.M. et al., "Anastrozole is superior to tamoxifen as first-line therapy for advanced breast cancer in postmenopausal women: results of a North American multicenter randomized trial. Arimidex Study Group" (2000) J Clin Oncol 18(22): 3758-3767.

Nanda R, Chow LQ, Dees EC, Berger R, Gupta S, Geva R, et al. Pembrolizumab in Patients With Advanced Triple-Negative Breast Cancer: Phase Ib Keynote-012 Study. J Clin Oncol. 2016;34(21):2460-7.

O'Neil, LA et al. "Therapeutic targeting of toll-like receptors for infectious and inflammatory diseases and cnacer." (2009) Pharmacol Rev 61:177-97.

(56) References Cited

OTHER PUBLICATIONS

Ono, Y. et al., "Phorbol ester binding to protein kinase C requires a cysteine-rich zinc-finger-like sequence" (1989) Proc. Natl. Acad. Sci. USA 86:4856-4871.
Osada, T et al. "Vaccination targeting human HER3 alters the phenotype of infiltrating T cells and respones to immune checkpoint inhibition." (2017). OncoImmunology 0(0).
Osada T, Yang XY, Hartman ZC, Glass O, Hodges BL, Niedzwiecki D, et al. Optimization of vaccine responses with an E1, E2b and E3-deleted Ad5 vector circumvents pre-existing anti-vector immunity. Cancer Gene Ther. 2009;16(9):673-82.
Pederson, MW et al. "Sym004: a novel synergistic anti-epidermal growth factor receptor antibody mixture with superior anticancer efficacy." (2010) Cancer Res 70:588-97.
Pulaski, BA et al. "Reduction of established spontaneous mammary carcinoma metastases following immunotherapy with major histocompatibility complex class II and B7.1 cell-based tumor vaccines." (1998) Cancer Res. 58:1486-93.
Renard, V. et al., "HER-2 DNA and Protein Vaccines Containing Potent Th Cell Epitopes Induce Distinct Protective and Therapeutic Antitumor Responses in HER-2 Transgenic Mice" (2003) J Immunol 171(3): 1588-1595.
Ren et al. "Polyclonal Her2-specific antibodies induced by vaccination mediate receptor internalization and degradation in tumor cells" (2012) Breast cancer research 14: R89.
Robinson et al. Activating ESR1 mutations in hormone-resistant metastatic breast cancer. Nature Genetics vol. 45, pp. 1446-1451 (2013).
Rosenberg, SA et al., Adoptive cell transfer: a clinical path to effective cancer immunotherapy. Nat. Rev. Cancer 8 (4): 299-308 (2008).
Sakai K, Yokote H, Murakami-Murofushi K, Tamura T, Saijo N, Nishio K. Pertuzumab, a novel HER dimerization inhibitor, inhibits the growth of human lung cancer cells mediated by the HER3 signaling pathway. Cancer Sci. 2007;98(9):1498-503.
Schoeberl, Birgit et al. "An ErbB3 Antibody, MM-121, Is Active in Cancers with Ligand-Dependent Activation" (2010) Cancer Research: 70(6): 2485-2494.
Soares KC, Rucki AA, Wu AA, Olino K, Xiao Q, Chai Y, et al. PD-1/PD-L1 blockade together with vaccine therapy facilitates effector T-cell infiltration into pancreatic tumors. J Immunother. 2015;38(1):1-11.
Tanaka, T. et al., "Efficient generation of antibodies to oncoproteins by using synthetic peptide antigens," (1985) Proc. Natl. Acad. Sci. USA 82:3400-3404.
Tiriveedhi V, Tucker N, Herndon J, Li L, Sturmoski M, Ellis M, Ma C, Naughton M, Lockhart AC, Gao F, et al. Safety and preliminary evidence of biologic efficacy of a mammaglobin—a DNA vaccine in patients with stable metastatic breast cancer. Clinical cancer research : an official journal of the American Association for Cancer Research. 2014;20(23):5964-75.
Topalian SL, Drake CG, Pardoll DM. Immune checkpoint blockade: a common denominator approach to cancer therapy. Cancer Cell. 2015;27(4):450-61.
Toy W. et al. ESR1 ligand-binding domain mutations in hormone-resistant breast cancer. Nat. Genetics 45(12), 2013.
Van Elsas A, Hurwitz AA, Allison JP. Combination immunotherapy of B16 melanoma using anti-cytotoxic T lymphocyte-associated antigen 4 (CTLA-4) and granulocyte/macrophage colony-stimulating factor (GM-CSF)—producing vaccines induces rejection of subcutaneous and metastatic tumors accompanied by autoimmune depigmentation. J Exp Med. 1999;190(3):355-66.
Weis et al. Constitutively active human estrogen receptors containing amino acid substitutions for tyrosine 537 in the receptor protein. Mol Endocrinol. Nov. 1996;10(11):1388-98.
Yoo, J.Y. et al., "Downregulation of ErbB3 Expression by Adenovirus Expressing ErbB3 Specific shRNA Enhances Antitumor Efficacy through Apoptosis Induction" (2009) Molecular Therapy: 17(Suppl. 1): S106.
Yuan, J. et al., "CTLA-4 blockade increases antigen-specific CD8(+) T cells in prevaccinated patients with melanoma: three cases" (2011) Cancer Immunol Immunother, 60(8): 1137-1146.
Yu, P et al. "Targeting the primary tumor to generate CTL for the effective eradication of spontaneous metastases." (2007) J Immunol 179:1960-8.
Zhang et al. An estrogen receptor mutant with strong hormone-independent activity from a metastatic breast cancer. Cancer Res. Apr. 1, 1997;57(7):1244-9.
Zitvogel, L et al. "The anticancer immune response: indispensable for therapeutic success?" (2008) 118:1991-2001.
International Search Report and Written Opinion for PCT/US2015/039367 dated Oct. 15, 2015 (13 pages).
Office Action for U.S. Appl. No. 15/324,183 dated Jan. 17, 2018 (12) pages.
Office Action for U.S. Appl. No. 15/324,183 dated Apr. 25, 2018 (14) pages.
Liddy et al., Monoclonal TCR-redirected tumor cell killing. Nature Med. 18:980-7 (2012).
Roskoski R, Jr. The ErbB/HER family of protein-tyrosine kinases and cancer. Pharmacological research : the official journal of the Italian Pharmacological Society. 2014;79:34-74.

\* cited by examiner

Figure 6
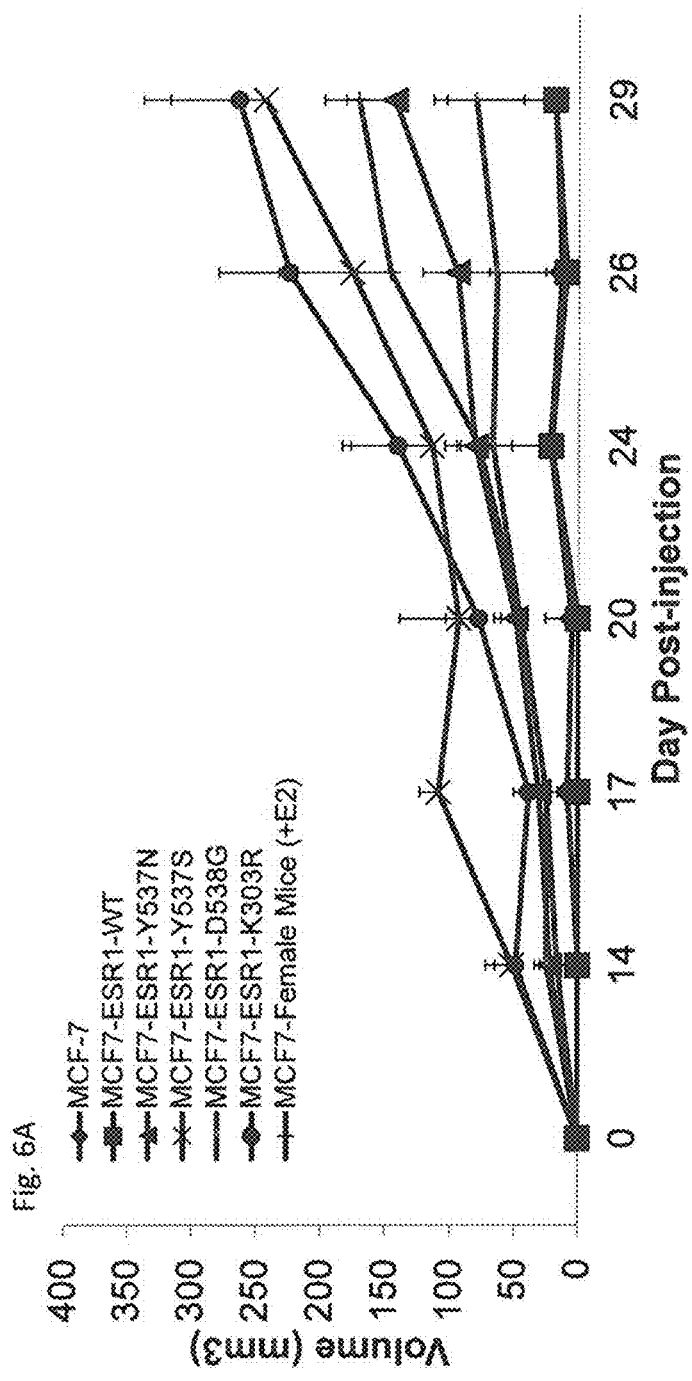
Fig. 6A
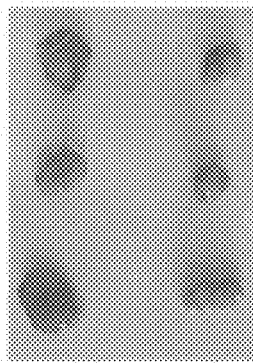
Fig. 6C
Fig. 6B
| Tumor Formation | Female Mice (+ E2) | Male Mice |
|---|---|---|
| MCF-7 | 9/10 | 2/10 |
| MCF-7-ESR1-WT |  | 2/5 |
| MCF7-ESR1-Y537N | 5/5 | 10/10 |
| MCF7-ESR1-Y537S |  | 5/5 |
| MCF7-ESR1-D538G |  | 4/5 |
| MCF7-ESR1-K303R |  | 5/5 |

Figure 9
Fig. 9A
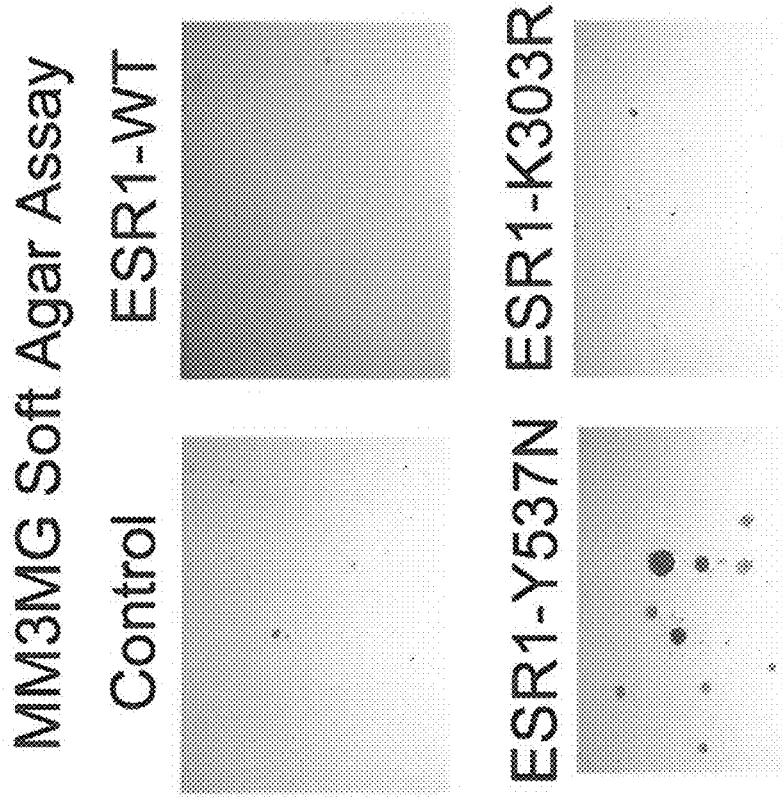
Fig. 9B
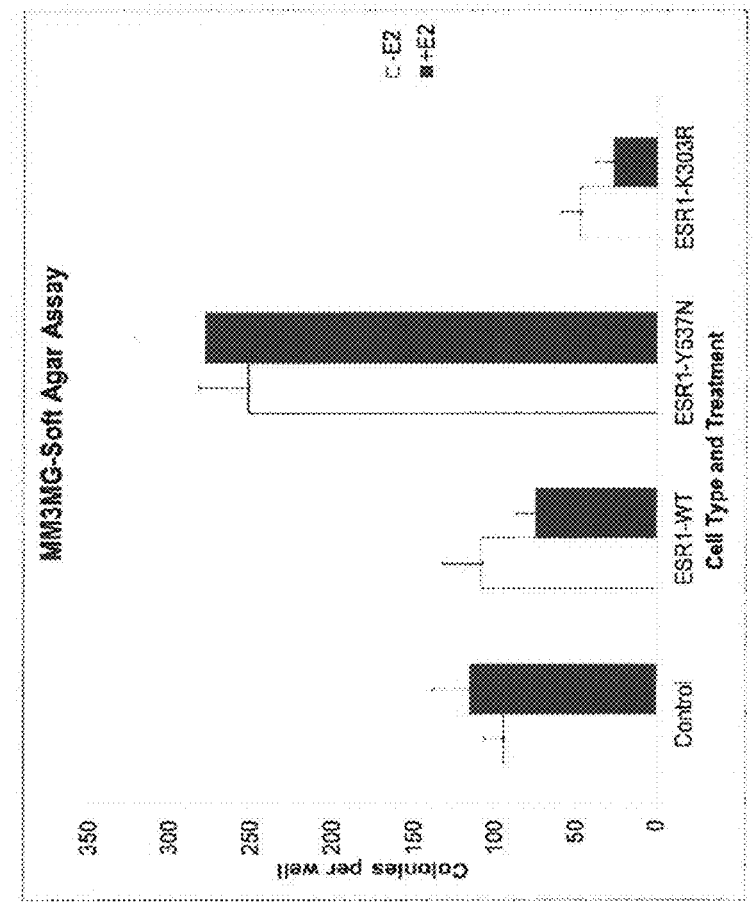

SEQUENCE LISTING

<160> NUMBER OF SEQ ID NOS: 25

<210> SEQ ID NO 1
<211> LENGTH: 595
<212> TYPE: PRT
<213> ORGANISM: Homo sapien

<400> SEQUENCE: 1

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
```

```
            100                 105                 110
Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
            130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                    165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
            210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
            290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
            515                 520                 525
```

```
Lys Cys Lys Asn Val Val Pro Leu Asn Asp Leu Leu Leu Glu Met Leu
        530             535             540

Asp Ala His Arg Leu His Ala Pro Thr Ser Arg Gly Gly Ala Ser Val
545             550             555             560

Glu Glu Thr Asp Gln Ser His Leu Ala Thr Ala Gly Ser Thr Ser Ser
                565             570             575

His Ser Leu Gln Lys Tyr Tyr Ile Thr Gly Glu Ala Glu Gly Phe Pro
            580             585             590

Ala Thr Val
        595

<210> SEQ ID NO 2
<211> LENGTH: 595
<212> TYPE: PRT
<213> ORGANISM: Homo sapien

<400> SEQUENCE: 2

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
```

```
                290                 295                 300
Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
            515                 520                 525

Lys Cys Lys Asn Val Val Pro Leu Ser Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 3
<211> LENGTH: 595
<212> TYPE: PRT
<213> ORGANISM: Homo sapien

<400> SEQUENCE: 3

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60
```

-continued

```
Ala Ala Ala Ala Asn Ala Gln Val Tyr Gly Gln Thr Gly Leu Pro Tyr
 65              70                  75                  80

Gly Pro Gly Ser Glu Ala Ala Phe Gly Ser Asn Gly Leu Gly Gly
                 85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
                115                 120                 125

Pro Tyr Tyr Leu Glu Asn Glu Pro Ser Gly Tyr Thr Val Arg Glu Ala
            130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
```

```
            485                 490                 495
Leu Gln Gln Gln His Gln Arg Leu Ala Gln Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Gly Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
    595

<210> SEQ ID NO 4
<211> LENGTH: 1788
<212> TYPE: DNA
<213> ORGANISM: Homo sapien

<400> SEQUENCE: 4
atgaccatga ccctccacac caaagcatcc gggatggccc tactgcatca gatccaaggg    60
aacgagctgg agcccctgaa ccgtccgcag ctcaagatcc cctggagcg ccccctgggc   120 gaggtgtacc tggacagcag caagcccgcc gtgtacaact accccgaggg cgccgcctac   180
gagttcaacg ccgcggccgc cgccaacgcg caggtctacg tcagaccgg cctcccctac   240 ggccccgggt ctgaggctgc ggcgttcggc tccaacggcc tggggggttt ccccccactc   300
aacagcgtgt ctccgagccc gctgatgcta ctgcacccgc cgccgcagct gtcgccttc    360 ctgcagcccc acggccagca ggtgccctac tacctggaga cgagcccag cggctacacg    420 gtgcgcgagg ccggcccgcc ggcattctac aggccaaatt cagataatcg acgccagggt   480
ggcagagaaa gattggccag taccaatgac aagggaagta tggctatgga atctgccaag   540
gagactcgct actgtgcagt gtgcaatgac tatgcttcag gctaccatta tggagtctgg   600
tcctgtgagg gctgcaaggc cttcttcaag agaagtattc aaggacataa cgactatatg   660
tgtccagcca ccaaccagtg caccattgat aaaaacagga ggaagagctg ccaggcctgc   720
cggctccgca atgctacga agtgggaatg atgaaaggtg ggatacgaaa agaccgaaga   780
ggagggagaa tgttgaaaca caagcgccag agagatgatg ggaggggcag gggtgaagtg   840
gggtctgctg agacatgag agctgccaac ctttggccaa gcccgctcat gatcaaacgc   900
tctaagagga cagcctggc cttgtccctg acggccgacc agatggtcag tgccttgttg   960
gatgctgagc cccgatact ctattccgag tatgatccta ccagacccct cagtgaagct  1020
tcgatgatgg gcttactgac caacctggca gacagggagc tggttcacat gatcaactgg  1080
gcgaagaggg tgccaggctt tgtggatttg accctccatg atcaggtcca ccttctagaa  1140
tgtgcctggc tagagatcct gatgattggt ctcgtctggc gctccatgga gcacccaggg  1200
aagctactgt ttgctcctaa cttgctcttg gacaggaacc aggaaaatg tgtagagggc  1260 atggtggaga tcttcgacat gctgctggct acatcatctc ggttccgcat gatgaatctg  1320
cagggagagg agtttgtgtg cctcaaatct attattttgc ttaattctgg agtgtacaca  1380
tttctgtcca gcaccctgaa gtctctggaa gagaaggacc atatccaccg agtcctggac  1440
```

-continued

```
aagatcacag acactttgat ccacctgatg gccaaggcag gcctgaccct gcagcagcag    1500
caccagcggc tggcccagct cctcctcatc ctctcccaca tcaggcacat gagtaacaaa    1560
ggcatggagc atctgtacag catgaagtgc aagaacgtgg tgccctcta tgacctgctg     1620 ctggagatgc tggacgccca ccgcctacat gcgcccacta gccgtggagg ggcatccgtg    1680
gaggagacgg accaaagcca cttggccact gcgggctcta cttcatcgca ttccttgcaa    1740
aagtattaca tcacggggga ggcagagggt ttccctgcca cagtctag               1788
```

<210> SEQ ID NO 5
<211> LENGTH: 595
<212> TYPE: PRT
<213> ORGANISM: Homo sapien

<400> SEQUENCE: 5

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Arg Asn
    290                 295                 300

Ser Leu Ala Leu Ser Leu Thr Ala Asp Gln Met Val Ser Ala Leu Leu
305                 310                 315                 320
```

```
Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 6
<211> LENGTH: 1239
<212> TYPE: PRT
<213> ORGANISM: Homo sapien

<400> SEQUENCE: 6

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
```

-continued

```
                    85                  90                  95
Gln Arg Leu Arg Ile Val Arg Gly Thr Gln Leu Phe Glu Asp Asn Tyr
            100                 105                 110
Ala Leu Ala Val Leu Asp Asn Gly Asp Pro Leu Asn Asn Thr Thr Pro
        115                 120                 125
Val Thr Gly Ala Ser Pro Gly Leu Arg Glu Leu Gln Leu Arg Ser
    130                 135                 140
Leu Thr Glu Ile Leu Lys Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
    210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
```

```
Gln Leu Cys Ala Arg Gly His Cys Trp Gly Pro Gly Thr Gln Cys
    515                 520                 525

Val Asn Cys Ser Gln Phe Leu Arg Gly Gln Glu Cys Val Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Pro Leu Thr Ser Ile Val Ser
625                 630                 635                 640

Ala Val Val Gly Ile Leu Leu Val Val Val Leu Gly Val Val Phe Gly
                645                 650                 655

Ile Leu Ile Lys Arg Arg Gln Gln Lys Ile Arg Lys Tyr Thr Met Arg
            660                 665                 670

Arg Leu Leu Gln Glu Thr Glu Leu Val Glu Pro Leu Thr Pro Ser Gly
            675                 680                 685

Ala Met Pro Asn Gln Ala Gln Met Arg Ile Leu Lys Glu Thr Glu Leu
690                 695                 700

Arg Lys Val Lys Val Leu Gly Ser Gly Ala Phe Gly Thr Val Tyr Lys
705                 710                 715                 720

Gly Ile Trp Ile Pro Asp Gly Glu Asn Val Lys Ile Pro Val Ala Ile
                725                 730                 735

Lys Val Leu Arg Glu Asn Thr Ser Pro Lys Ala Asn Lys Glu Ile Leu
            740                 745                 750

Asp Glu Ala Tyr Val Met Ala Gly Val Gly Ser Pro Tyr Val Ser Arg
            755                 760                 765

Leu Leu Gly Ile Cys Leu Thr Ser Thr Val Gln Leu Val Thr Gln Leu
            770                 775                 780

Met Pro Tyr Gly Cys Leu Leu Asp His Val Arg Glu Asn Arg Gly Arg
785                 790                 795                 800

Leu Gly Ser Gln Asp Leu Leu Asn Trp Cys Met Gln Ile Ala Lys Gly
                805                 810                 815

Met Ser Tyr Leu Glu Asp Val Arg Leu Val His Arg Asp Leu Ala Ala
            820                 825                 830

Arg Asn Val Leu Val Lys Ser Pro Asn His Val Lys Ile Thr Asp Phe
            835                 840                 845

Gly Leu Ala Arg Leu Leu Asp Ile Asp Glu Thr Glu Tyr His Ala Asp
            850                 855                 860

Gly Gly Lys Val Pro Ile Lys Trp Met Ala Leu Glu Ser Ile Leu Arg
865                 870                 875                 880

Arg Arg Phe Thr His Gln Ser Asp Val Trp Ser Tyr Gly Val Thr Val
                885                 890                 895

Trp Glu Leu Met Thr Phe Gly Ala Lys Pro Tyr Asp Gly Ile Pro Ala
            900                 905                 910

Arg Glu Ile Pro Asp Leu Leu Glu Lys Gly Glu Arg Leu Pro Gln Pro
            915                 920                 925
```

```
Pro Ile Cys Thr Ile Asp Val Tyr Met Ile Met Val Lys Cys Trp Met
    930                 935                 940

Ile Asp Ser Glu Cys Arg Pro Arg Phe Arg Glu Leu Val Ser Glu Phe
945                 950                 955                 960

Ser Arg Met Ala Arg Asp Pro Gln Arg Phe Val Val Ile Gln Asn Glu
                965                 970                 975

Asp Leu Gly Pro Ala Ser Pro Leu Asp Ser Thr Phe Tyr Arg Ser Leu
            980                 985                 990

Leu Glu Asp Asp Asp Met Gly Asp  Leu Val Asp Ala Glu  Glu Tyr Leu
        995                 1000                 1005

Val Pro Gln Gln Gly Phe Phe  Cys Pro Asp Pro Ala  Pro Gly Ala
    1010                1015                1020

Gly Gly Met Val His His Arg  His Arg Ser Ser Ser  Thr Arg Ser
    1025                1030                1035

Gly Gly Gly Asp Leu Thr Leu  Gly Leu Glu Pro Ser  Glu Glu Glu
    1040                1045                1050

Ala Pro Arg Ser Pro Leu Ala  Pro Ser Glu Gly Ala  Gly Ser Asp
    1055                1060                1065

Val Phe Asp Gly Asp Leu Gly  Met Gly Ala Ala Lys  Gly Leu Gln
    1070                1075                1080

Ser Leu Pro Thr His Asp Pro  Ser Pro Leu Gln Arg  Tyr Ser Glu
    1085                1090                1095

Asp Pro Thr Val Pro Leu Pro  Ser Glu Thr Asp Gly  Tyr Val Ala
    1100                1105                1110

Pro Leu Thr Cys Ser Pro Gln  Pro Glu Tyr Val Asn  Gln Pro Asp
    1115                1120                1125

Val Arg Pro Gln Pro Pro Ser  Pro Arg Glu Gly Pro  Leu Pro Ala
    1130                1135                1140

Ala Arg Pro Ala Gly Ala Thr  Leu Glu Arg Ala Lys  Thr Leu Ser
    1145                1150                1155

Pro Gly Lys Asn Gly Val Val  Lys Asp Val Phe Ala  Phe Gly Gly
    1160                1165                1170

Ala Val Glu Asn Pro Glu Tyr  Leu Thr Pro Gln Gly  Gly Ala Ala
    1175                1180                1185

Pro Gln Pro His Pro Pro Pro  Ala Phe Ser Pro Ala  Phe Asp Asn
    1190                1195                1200

Leu Tyr Tyr Trp Asp Gln Asp  Pro Pro Glu Arg Gly  Ala Pro Pro
    1205                1210                1215

Ser Thr Phe Lys Gly Thr Pro  Thr Ala Glu Asn Pro  Glu Tyr Leu
    1220                1225                1230

Gly Leu Asp Val Pro Val
    1235

<210> SEQ ID NO 7
<211> LENGTH: 111
<212> TYPE: PRT
<213> ORGANISM: Homo sapien

<400> SEQUENCE: 7

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45
```

```
Leu Tyr Gln Gly Cys Gln Val Val Gln Gly Asn Leu Glu Leu Thr Tyr
         50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn
            100                 105                 110
```

<210> SEQ ID NO 8
<211> LENGTH: 668
<212> TYPE: PRT
<213> ORGANISM: Homo sapien

<400> SEQUENCE: 8

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                 20                  25                  30

Leu Arg Leu Pro Ala Ser Pro Glu Thr His Leu Asp Met Leu Arg His
             35                  40                  45

Leu Tyr Gln Gly Cys Gln Val Val Gln Gly Asn Leu Glu Leu Thr Tyr
         50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
```

Glu Val Thr Ala Glu Asp Gly Thr Gln Arg Cys Glu Lys Cys Ser Lys
305                 310                 315                 320
                        325                     330                     335

Pro Cys Ala Arg Val Cys Tyr Gly Leu Gly Met Glu His Leu Arg Glu
                        340                     345                     350

Val Arg Ala Val Thr Ser Ala Asn Ile Gln Glu Phe Ala Gly Cys Lys
                        355                     360                     365

Lys Ile Phe Gly Ser Leu Ala Phe Leu Pro Glu Ser Phe Asp Gly Asp
                370                     375                     380

Pro Ala Ser Asn Thr Ala Pro Leu Gln Pro Glu Gln Leu Gln Val Phe
385                     390                     395                     400

Glu Thr Leu Glu Glu Ile Thr Gly Tyr Leu Tyr Ile Ser Ala Trp Pro
                        405                     410                     415

Asp Ser Leu Pro Asp Leu Ser Val Phe Gln Asn Leu Gln Val Ile Arg
                        420                     425                     430

Gly Arg Ile Leu His Asn Gly Ala Tyr Ser Leu Thr Leu Gln Gly Leu
                        435                     440                     445

Gly Ile Ser Trp Leu Gly Leu Arg Ser Leu Arg Glu Leu Gly Ser Gly
                450                     455                     460

Leu Ala Leu Ile His His Asn Thr His Leu Cys Phe Val His Thr Val
465                     470                     475                     480

Pro Trp Asp Gln Leu Phe Arg Asn Pro His Gln Ala Leu Leu His Thr
                        485                     490                     495

Ala Asn Arg Pro Glu Asp Glu Cys Val Gly Glu Gly Leu Ala Cys His
                        500                     505                     510

Gln Leu Cys Ala Arg Gly His Cys Trp Gly Pro Gly Pro Thr Gln Cys
                        515                     520                     525

Val Asn Cys Ser Gln Phe Leu Arg Gly Gln Glu Cys Val Glu Glu Cys
                530                     535                     540

Arg Val Leu Gln Gly Leu Pro Arg Glu Tyr Val Asn Ala Arg His Cys
545                     550                     555                     560

Leu Pro Cys His Pro Glu Cys Gln Pro Gln Asn Gly Ser Val Thr Cys
                        565                     570                     575

Phe Gly Pro Glu Ala Asp Gln Cys Val Ala Cys Ala His Tyr Lys Asp
                        580                     585                     590

Pro Pro Phe Cys Val Ala Arg Cys Pro Ser Gly Val Lys Pro Asp Leu
                        595                     600                     605

Ser Tyr Met Pro Ile Trp Lys Phe Pro Asp Glu Glu Gly Ala Cys Gln
                610                     615                     620

Pro Cys Pro Ile Asn Cys Thr His Ser Pro Leu Thr Ser Ile Val Ser
625                     630                     635                     640

Ala Val Val Gly Ile Leu Leu Val Val Leu Gly Val Val Phe Gly
                        645                     650                     655

Ile Leu Ile Lys Arg Arg Gln Gln Lys Ile Arg Lys
                660                     665

<210> SEQ ID NO 9
<211> LENGTH: 331
<212> TYPE: PRT
<213> ORGANISM: Homo sapien

<400> SEQUENCE: 9

Met Arg Ala Asn Asp Ala Leu Gln Val Leu Gly Leu Leu Phe Ser Leu
1               5                   10                  15

```
Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
 50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
 130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
 210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
 290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330
```

<210> SEQ ID NO 10
<211> LENGTH: 1342
<212> TYPE: PRT
<213> ORGANISM: Homo sapien

<400> SEQUENCE: 10

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
 50                  55                  60
```

```
Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Arg Gly Thr Gln Val Tyr Asp
                100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
        130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
        450                 455                 460

His His Ser Leu Asn Trp Thr Lys Val Leu Arg Gly Pro Thr Glu Glu
465                 470                 475                 480
```

```
Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
        500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Cys Pro His Gly
        580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
            645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
            725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
        770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
            805                 810                 815

Gln Ile Ala Lys Gly Met Tyr Tyr Leu Glu Glu His Gly Met Val His
        820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
            885                 890                 895

Tyr Gly Val Thr Val Trp Glu Leu Met Thr Phe Gly Ala Glu Pro Tyr
```

```
                    900             905                 910
Ala Gly Leu Arg Leu Ala Glu Val Pro Asp Leu Leu Glu Lys Gly Glu
            915                 920                 925

Arg Leu Ala Gln Pro Gln Ile Cys Thr Ile Asp Val Tyr Met Val Met
930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
            995                 1000                1005

Leu Asp Leu Asp Leu Asp Leu Glu Ala Glu Glu Asp Asn Leu Ala
    1010                1015                1020

Thr Thr Thr Leu Gly Ser Ala Leu Ser Leu Pro Val Gly Thr Leu
    1025                1030                1035

Asn Arg Pro Arg Gly Ser Gln Ser Leu Leu Ser Pro Ser Ser Gly
    1040                1045                1050

Tyr Met Pro Met Asn Gln Gly Asn Leu Gly Gly Ser Cys Gln Glu
    1055                1060                1065

Ser Ala Val Ser Gly Ser Ser Glu Arg Cys Pro Arg Pro Val Ser
    1070                1075                1080

Leu His Pro Met Pro Arg Gly Cys Leu Ala Ser Glu Ser Ser Glu
    1085                1090                1095

Gly His Val Thr Gly Ser Glu Ala Glu Leu Gln Glu Lys Val Ser
    1100                1105                1110

Met Cys Arg Ser Arg Ser Arg Ser Arg Ser Pro Arg Pro Arg Gly
    1115                1120                1125

Asp Ser Ala Tyr His Ser Gln Arg His Ser Leu Leu Thr Pro Val
    1130                1135                1140

Thr Pro Leu Ser Pro Pro Gly Leu Glu Glu Glu Asp Val Asn Gly
    1145                1150                1155

Tyr Val Met Pro Asp Thr His Leu Lys Gly Thr Pro Ser Ser Arg
    1160                1165                1170

Glu Gly Thr Leu Ser Ser Val Gly Leu Ser Ser Val Leu Gly Thr
    1175                1180                1185

Glu Glu Glu Asp Glu Asp Glu Glu Tyr Glu Tyr Met Asn Arg Arg
    1190                1195                1200

Arg Arg His Ser Pro Pro His Pro Pro Arg Pro Ser Ser Leu Glu
    1205                1210                1215

Glu Leu Gly Tyr Glu Tyr Met Asp Val Gly Ser Asp Leu Ser Ala
    1220                1225                1230

Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305
```

```
Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 11
<211> LENGTH: 9
<212> TYPE: PRT
<213> ORGANISM: Homo sapien

<400> SEQUENCE: 11

Ile Gln Gly Asn Glu Leu Glu Pro Leu
1               5

<210> SEQ ID NO 12
<211> LENGTH: 9
<212> TYPE: PRT
<213> ORGANISM: Homo sapien

<400> SEQUENCE: 12

Phe Met Val Leu Gln Val Ile Lys Phe
1               5

<210> SEQ ID NO 13
<211> LENGTH: 8
<212> TYPE: PRT
<213> ORGANISM: Homo sapien

<400> SEQUENCE: 13

Leu Glu Met Leu Glu Ala Lys Val
1               5

<210> SEQ ID NO 14
<211> LENGTH: 8
<212> TYPE: PRT
<213> ORGANISM: Homo sapien

<400> SEQUENCE: 14

Glu Val Phe Leu Pro Gln Arg Ala
1               5

<210> SEQ ID NO 15
<211> LENGTH: 9
<212> TYPE: PRT
<213> ORGANISM: Homo sapien

<400> SEQUENCE: 15

Ile Phe Leu Asn Thr Glu Val Ser Leu
1               5

<210> SEQ ID NO 16
<211> LENGTH: 9
<212> TYPE: PRT
<213> ORGANISM: Homo sapien

<400> SEQUENCE: 16

Leu Thr Ala Glu Glu Thr Asp Lys Ile
1               5

<210> SEQ ID NO 17
<211> LENGTH: 10
```

```
<212> TYPE: PRT
<213> ORGANISM: Homo sapien

<400> SEQUENCE: 17

Leu Thr Ser Ser Ser Ile Asp Pro Gly Leu
1               5                   10

<210> SEQ ID NO 18
<211> LENGTH: 9
<212> TYPE: PRT
<213> ORGANISM: Homo sapien

<400> SEQUENCE: 18

Met Leu Lys His Lys Arg Pro Leu Ala
1               5

<210> SEQ ID NO 19
<211> LENGTH: 10
<212> TYPE: PRT
<213> ORGANISM: Homo sapien

<400> SEQUENCE: 19

Thr Ile Val Ser Leu Asp Ala Ala Arg Arg
1               5                   10

<210> SEQ ID NO 20
<211> LENGTH: 9
<212> TYPE: PRT
<213> ORGANISM: Homo sapien

<400> SEQUENCE: 20

Lys Gly Asp Glu Glu Lys Glu Asn Asn
1               5

<210> SEQ ID NO 21
<211> LENGTH: 9
<212> TYPE: PRT
<213> ORGANISM: Homo sapien

<400> SEQUENCE: 21

Leu Cys Val Lys Ala Met Ile Leu Leu
1               5

<210> SEQ ID NO 22
<211> LENGTH: 9
<212> TYPE: PRT
<213> ORGANISM: Homo sapien

<400> SEQUENCE: 22

Met Asn Gln Lys Leu Ser Pro Phe Met
1               5

<210> SEQ ID NO 23
<211> LENGTH: 8
<212> TYPE: PRT
<213> ORGANISM: Homo sapien

<400> SEQUENCE: 23

Arg Tyr Lys Lys Leu Lys Val Glu
1               5

<210> SEQ ID NO 24
<211> LENGTH: 10
<212> TYPE: PRT
<213> ORGANISM: Homo sapien
```

```
<400> SEQUENCE: 24

Ser Lys Ala Lys Ser Leu Thr Asp Pro Ser
1               5                   10

<210> SEQ ID NO 25
<211> LENGTH: 8
<212> TYPE: PRT
<213> ORGANISM: Homo sapien

<400> SEQUENCE: 25

Trp Phe Gly Ile Lys Ala Pro Glu
1               5
```

VACCINES AGAINST AN ONCOGENIC ISOFORM OF ESR1 AND METHODS OF USING THE SAME

CROSS-REFERENCE TO RELATED APPLICATIONS

This patent application is a divisional of U.S. patent application Ser. No. 15/324,183, filed Jan. 5, 2017, which is a national stage filing under 35 U.S.C. § 371 of International Application No. PCT/US2015/039367, filed Jul. 7, 2015, which claims the benefit of priority of U.S. Provisional Patent Application No. 62/021,586, filed Jul. 7, 2014, which are incorporated herein by reference in their entireties.

STATEMENT REGARDING FEDERALLY SPONSORED RESEARCH

This invention was made with United States government support awarded by the Department of Defense grant number BC 13107. The United States has certain rights in this invention.

SEQUENCE LISTING

A Sequence Listing accompanies this application and is incorporated herein by reference in its entirety. The Sequence Listing was filed with the application as a text file on Jul. 7, 2015.

INTRODUCTION

This application relates to a cancer vaccine against ESR1, specifically a vaccine against ESR1 isoform antigens that are expressed on cancer cells or in response to development of resistance to a therapeutic intervention to cancer (or pre-cancers). Methods of using the vaccines are also provided.

Cancer vaccines target antigens expressed by tumors, but application of these vaccines has not been as effective as once hoped due to induction of immune tolerance by chronic overexpression of the targeted protein in the absence of co-stimulatory molecules and the induction of an immuno-modulatory environment. Preventative cancer vaccines may be more promising, but cancers are highly variable, with multiple genetic changes, but few truly universal changes. Thus, it is difficult to predict what antigens will be overexpressed on any specific cancer or whether an individual should be vaccinated and if so, with what antigens. In contrast, a strategy is proposed here in which vaccination against the antigen(s) that will predictably be overexpressed in response to a therapy, but prior to that antigen's overexpression by the cancer cells is used to induce a robust anti-cancer immune response.

SUMMARY

Provided herein is a mechanism of revolutionizing cancer therapy or prevention by preventing the development of resistance to cancer therapeutic or cancer prevention agents by identifying which antigens are likely to be expressed in a cancer or precancer in response to treatment with a cancer therapeutic or prevention agent and thus which antigens may be targeted with a vaccine in patients.

A vaccine targeting a specific antigen involved in a resistance mechanism, namely ESR1, and methods of using the vaccine are provided. In one aspect, the vaccine includes a polynucleotide encoding an ESR1 polypeptide, a mutant of an ESR1 polypeptide, or a portion of an ESR1 polypeptide. For example, ESR1 polypeptides of SEQ ID NO: 1-3 or 5 or portions thereof may be included in a vaccine as detailed below. SEQ ID NO: 1-3 and 5 each provide single amino acid substitution mutants of ESR1. SEQ ID NO: 1 is an ESR1 polypeptide with an Y537N mutation. SEQ ID NO: 2 is an ESR1 polypeptide with a Y537S mutation. SEQ ID NO: 3 is an ESR1 polypeptide with a D538G mutation. SEQ ID NO: 5 is an ESR1 polypeptide with a K303R mutation.

In another aspect, methods of treating a cancer or precancer or reducing the likelihood of the cancer or precancer to develop resistance to a cancer therapeutic or prevention agent by administering the vaccine provided herein to a subject with cancer or precancer are provided. The vaccine may be administered before, concurrently with or after administration of the cancer therapeutic or prevention agent. The vaccine may also be administered before, concurrently with or after administration of checkpoint inhibitory immunomodulatory agents such as antagonistic antibodies specific for CTLA-4 or PD1.

BRIEF DESCRIPTION OF THE DRAWINGS

FIG. 6 is a set of figures showing that ESR1-mutants can confer estrogen-independent growth in ER+ breast cancer in vivo. Stably infected MCF-7 cells were injected into the flank of SCID-Beige male mice (or female where indicated) at a concentration of 1M cells in 100 µl of PBS at Day 0. In female control group, a 17B-Estradiol pellet (60 day release, Innovative Research of America, Sarasota Fla.) was also implanted. Tumor growth was then monitored as indicated by caliper measurement (N=5 or 10 per group, bars represent SE) and is shown in the graph (FIG. 6A) and reported in the table (FIG. 6B). The photograph at the bottom right of the figure (FIG. 6C) is from a previous experiment measuring the growth of MCF-7-ESR1-Y537N cells in female mice supplemented with 17B-Estradiol pellets (top) versus male mice without supplementation (bottom).

FIG. 9 is a set of figures showing that ESR1 mutants in murine mammary cells can confer an advantage in anchorage-independent growth. MM3MG cells stably expressing the indicated genes were plated in 12-well dishes plates (2,500 per well) and assessed at 3 weeks days post-plating at 4× and 10× magnification (N=4, bars indicate SD). FIG. 9A is a graph showing the number of colonies per well for cells expressing the indicated ESR1 protein and either exposed to eatrogen or not. FIG. 9B is a set of photographs showing anchorage independent cell growth of the indicated cells.

DETAILED DESCRIPTION

Figure 1:
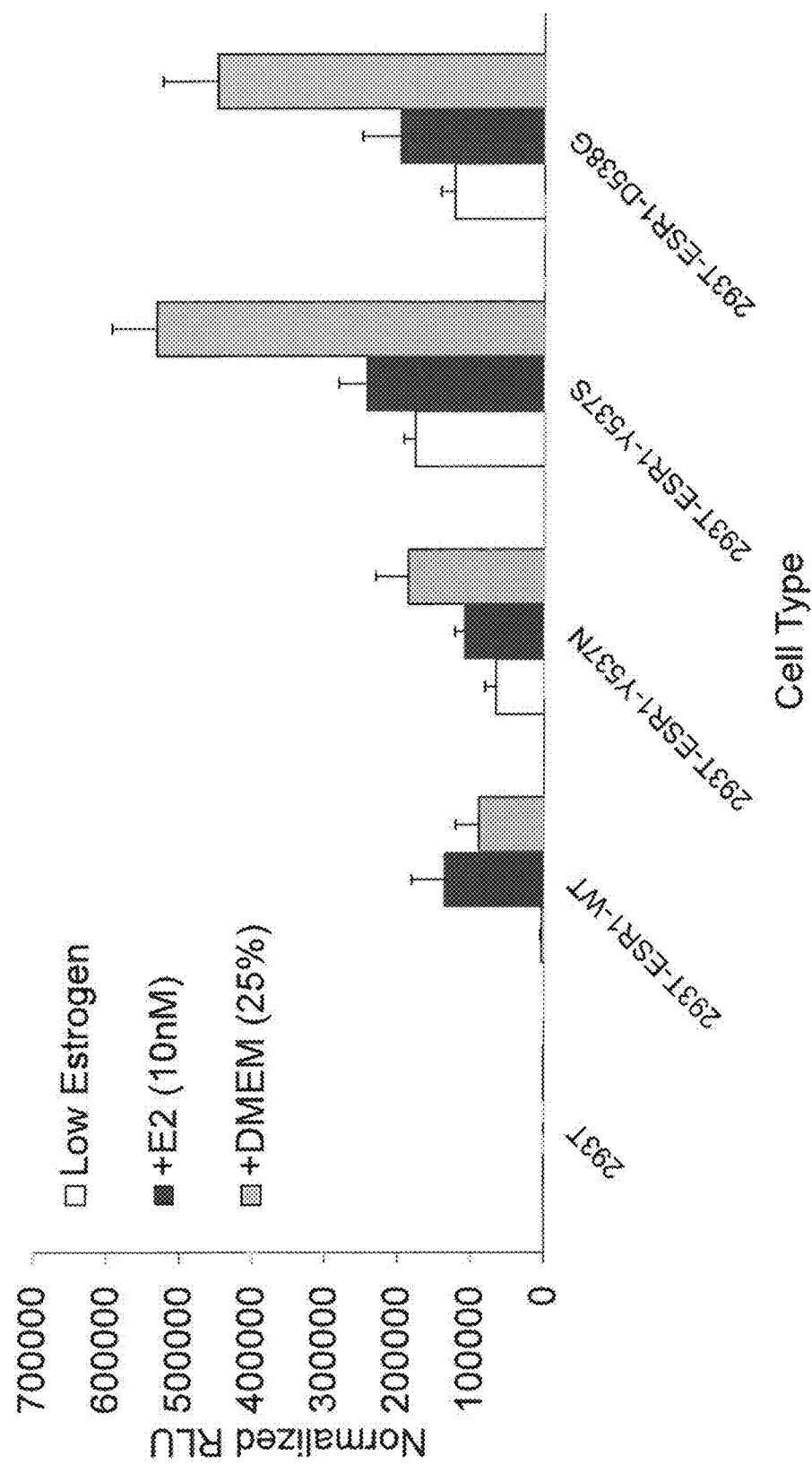
FIG. 1 is a graph showing that ESR1 mutants can confer ER Signaling in the absence of estrogen stimulation. 293T cells stably expressing the indicated genes were transfected with an ERE luciferase reporter (180 ng), along with a LacZ control (20 ng) and plated in 96 well plates (20,000 cells per well). At 24 hours post-transfection, cells were lysed and luciferase activity measured (normalized to LacZ transfection control). N=4 per group.

Approximately 70% of all breast cancers are classified as estrogen receptor positive (ER+); dependent upon constitutive estrogen receptor signaling[6]. Although different classes of endocrine (anti-estrogen) therapies (including selective estrogen receptor modulators (SERMS), downregulators, and aromatase inhibitors (AIs)) are effective treatments for these cancers in adjuvant settings, approximately 50% of women will eventually relapse and die from metastatic ER+ disease[7-9]. Thus, despite the advent of newer therapies (such as AIs) there remains an unrelenting rate of recurrence in ER+ breast cancer, particularly in cases where metastasis has occurred[10-12]. Significantly, all patients that develop metastatic ER+ disease will progress to an endocrine therapy resistant disease. At this stage, there is no cure for ER+ breast cancer. Because compensatory mechanisms appear to account for resistance that develops in a significant percentage of anti-estrogen treated patients, we propose a novel approach that has the potential to target critical driver mutations for the lifetime of the patient. Provided herein is specifically targeted immunotherapy directed toward specific resistance drivers that are predictably evoked by compensatory resistance mechanisms.

As a novel alternative to vaccines targeting well established tumor antigens, we hypothesized that the antigen-specific immune non-responsiveness to conventional tumor-associated antigens may be avoided by targeting tumor antigens that are induced after exposure to a cancer therapeutic or prevention agent as a mechanism of developing therapeutic resistance. Although there may be many potential antigens overexpressed in response to a cancer therapeutic or prevention agent, those antigens that are likely critical components of specific therapeutic resistance mechanisms would be attractive targets, as immunologic ablation of clones expressing such antigens should eliminate the clinical recurrence of therapy resistant tumor cells. One such antigen thought to be essential to therapeutic resistance is the estrogen receptor, ESR1. As proof of this concept in ER+ breast cancer, we have chosen to focus this approach on the recently uncovered resistance mutations to Estrogen Receptor alpha (ESR1).

We recently demonstrated that polyclonal antibodies induced by vaccination against receptors such as HER2 and HER3 can mediate profound receptor internalization and degradation, providing a therapeutic effect in vitro and in vivo (Ren et al., Breast Cancer Research 2012 14: R89 and International Patent Application No. WO 2013/110030, both of which are incorporated herein by reference in their entireties).

A vaccine composed of single or multiple forms of the ESR1 gene (Estrogen Receptor alpha) encoded by a platform that would elicit an immune response to the wild type or mutated epitopes of ESR1 is provided herein. In one embodiment, vaccines comprising one or more (or all) or portions of one or more (or all) of SEQ ID NOs: 1-3 and SEQ ID NO: 5 are provided. In the Examples, each vaccine contained a single ESR1 mutant, but more than one mutant can be included in a single vaccine. While others have utilized different approaches to target wild-type ESR1 through vaccination, our approach would selectively target forms of this gene that enable endocrine therapy resistance in tumors, i.e. mutant forms of ESR1 that allow the cancer cells to escape a therapeutic agent and continue growth. As such, we would expect that targeting these forms would prevent their emergence and would effectively prevent the development of resistance to endocrine therapies in ER+ breast cancer as well as other endocrine dependent cancers. Additionally, selectively targeting this specific mutant form of ESR1 would allow for effective tumor-specific anti-cancer activity mediated through immune targeting.

This invention would optimally be utilized through the inclusion of antigens encoded by the wild type and/or mutant forms of ESR1 gene (Y537N, Y537S, D538G, K303R and others), optimized forms of this gene (truncated, inactivated or otherwise), or specific combinations of peptide/epitopes of this gene in different immune stimulatory vector systems. The mutant forms of ESR1 gene (Y537N, Y537S, D538G, K303R) are provided as SEQ ID NOs; 1-3 and 5, respectively. Portions of these polypeptides may also be included in the vaccine. Suitably the portion included in the vaccine includes the mutation at the indicated amino acid. The portion included in the vaccine may include the mutation at only one of 537, 538 or 303 or may include small peptide epitopes comprising two of more of these mutations. The vaccine may include further peptides with additional mutations in the ESR1 protein in addition to those identified herein. The B and T cell epitopes being recognized after vaccination in the examples have not been identified, but those of skill in the art would expect the epitopes to be 6, 8, 10, 12, 14, 16, 18 or 20 amino acids in length. The Examples do suggest that the epitope includes the mutation at 537 for the vaccine containing SEQ ID NO:1 as the immune response generated after vaccination with the vaccine comprising SEQ ID NO: 1 did not recognize wild-type ESR1. The vaccines used in the Examples encompass larger polypeptides, but vaccines may include smaller portions of the ESR1 polypeptides than those provided herein. Suitably the vaccines include the region flanking the mutations at amino acid 537, 538 or 303 of the sequences and include at least 8, 10, 12, 14, 16, 18, 20 or more amino acids.

A polynucleotide encoding a polypeptide of SEQ ID NO: 1-3 or 5 or a portion thereof may be encompassed in a vaccine vector. Suitable vaccine vectors include, but are not limited to viral vectors such as adenoviral, fowlpox, vaccinia, VEE, etc., DNA-based vaccination vectors, or protein/peptide vaccination strategies. Liposomes or bacterial vaccine vectors may also be suitable. This immunotherapeutic platform could be used prior to the development of cancer types prior to the development of endocrine resistance, used in front line or adjuvant settings as a treatment for these cancers, and also as a preventative measure to prohibit the development and evolution of this signaling pathway as a resistance pathway.

The vaccines or vaccine vectors may include polynucleotides encoding additional polypeptides, such as HER3, HER2 or polypeptides of either of these comprising mutations such as those provided in SEQ ID NOs: 6-10 or any of the epitopes provided in International Publication No. WO2013/110030, which is incorporated herein by reference in its entirety. The vaccines or vaccine vectors may also include or be administered in conjunction with a checkpoint inhibitory immunomodulatory agent. The checkpoint inhibitory immunomodulatory agent may be an antibody antagonistic for CTLA-4 or PD1. In the Examples a PD1 antibody obtained from BioXCell called RMP1-14 and a CTLA-4 antibody from BioXCell called 9D9 were used. Other similar antibodies are commercially available or in clinical trials such as ipilimumab and nivolumab.

This would be easily distinguished from our and other prior approaches targeting wild-type ESR1 as the mutations to different portions of this gene render them insensitive to endocrine-targeted therapies with enhanced oncogenic potential. As such, vaccines targeting these mutant forms may elicit a different epitope repertoire for immune targeting and potentially a more significant anti-tumor effect by specifically targeting the development of endocrine resistance and specifically preventing it through immunoselective pressure.

Generation of resistance to cancer therapeutic or prevention agents is a common problem in the treatment of cancer or precancer and in several cases the mechanism of resistance to the therapeutic agent is known. Resistance is often the result of changes in gene expression (over-expression or blocked expression of a protein), change in the gene by mutation, or altered sequences by altered splicing or translocation or altered activation of a protein in the cells (over-activation or blocked activation of a protein).

In those cases where over-expression or over-activation of a protein, or a new sequence in the protein is responsible for increasing the resistance of the cancer or precancer cells to the therapeutic or prevention agent, we report a method for reducing the likelihood that the cancer or precancer will develop resistance to the cancer therapeutic or prevention agent. As used herein, resistance to a cancer therapeutic or prevention agent indicates that the cancer therapeutic or prevention agent is not as effective at inhibiting the growth of, or killing, cancer or precancer cells in response to the cancer therapeutic or prevention agent. The method may even block the development of resistance to the cancer therapeutic or prevention agent or may reverse resistance to the cancer therapeutic or prevention agent after it has developed. The methods include administering the cancer therapeutic or prevention agent and administering a vaccine to the subject in need of treatment for a cancer. The vaccine comprises a polynucleotide encoding a polypeptide whose expression or activation is correlated with or results in development of resistance of the cancer or precancer to the cancer therapeutic or prevention agent. The vaccines provided herein include an ESR1 polypeptide or a polynucleotide encoding an ESR1 polypeptide such as the polypeptide of SEQ ID NO: 2, 4, or 6.

The vaccine may be administered before, during or after treatment with a cancer therapeutic or prevention agent or may be administered simultaneously with the cancer therapeutic or prevention agent. The administration of the vaccine and the cancer therapeutic or prevention agent to the subject reduces the likelihood that the subject's cancer or precancer will develop resistance to the therapeutic or prevention agent as compared to a control subject with a similar cancer or precancer not administered the vaccine or as compared to the general likelihood of a population of subjects having the cancer or precancer. In some embodiments, the cancer or precancer in individuals administered both the vaccine and the therapeutic or prevention agent does not develop resistance to the cancer therapeutic or prevention agent and is treated. Alternatively, the growth of the cancer or precancer may be inhibited or the growth rate reduced. The administration of the vaccine and cancer therapeutic or prevention agent may also reverse resistance to the cancer therapeutic or prevention agent if the cancer or precancer is already resistant to the cancer therapeutic or prevention agent. In some embodiments, administration of the vaccine is sufficient to treat the cancer or inhibit the growth or kill the cancer. In other embodiments, the vaccine must be administered in conjunction with the cancer therapeutic or prevention agent or prior to development of resistance to the cancer therapeutic or prevention agent by the cancer.

The vaccine may include a polynucleotide encoding an ESR1 polypeptide. Three point mutations (4 mutant forms) of ESR1 associated with resistance to cancer therapeutic agents are provided as SEQ ID NOs: 1-3 and 5. The vaccine may comprise full-length ESR1 or portions thereof. For example, the vaccine may comprise only the epitopes identified in the examples or peptides comprising the mutations or deletions associated with resistance. Suitably the vaccine is capable of eliciting an immune response to ESR1 in a subject administered the vaccine. The immune response may be a B cell or T cell response. Suitably the immune response includes an antibody response directed to ESR1. The immune response may be a polyclonal antibody response in which multiple epitopes of ESR1 are recognized by antibodies. The immune response may recognize an epitope including the mutations such that after immunization the wild-type protein is not recognized or not recognized as strongly as the mutant form.

ESR1, as shown in SEQ ID NOs: 1-3 and 5, comprises mutations as indicated that lead to endocrine resistance. The mutations result in a unique sequence in the peptide and epitopes spanning these mutations can be identified and antibodies generated using the vaccines described herein. Those of skill in the art will appreciate that a vaccine including polynucleotides encoding only portions of full-length ESR1, i.e. antigenic epitopes, may be used in the vaccines described herein. Portions of the ESR1 including the mutation sites can be included in the vaccine. We have the following isolated ESR and ESR related peptides presented by MHC molecules on tumor cells.

TABLE 1

T cell epitopes derived from estrogen receptor related proteins:

| MCF10 (SEQ ID NO:) | | |
|---|---|---|
| IQGNELEPL (11) | A2 | Estrogen receptor ESR1 |
| MCF7 | | |
| FMVLQVIKT (12) | A24 | nuclear receptor subfamily I group I member 3 isoform 15 |
| LEMLEAKV (13) | non A2/A24 | estrogen-related receptor beta |
| MDA | | |
| EVFLPQRA (14) | A2 | estrogen-related receptor beta |
| IFLNTEVSL (15) | A24 | estrogen receptor coactivator |
| LTAEETDKI (16) | A2/A24 | estrogen receptor coactivator |
| LTSSSIDPGL (17) | A2 | estrogen receptor binding protein variant |
| MLKHKRPLA (18) | A2/A24 | estrogen receptor alpha splice variant, partial |
| TIVSLDAARR (19) | A2 | estrogen-responsive B box protein |

TABLE 1 -continued

T cell epitopes derived from estrogen receptor related proteins:

| KGDEEKENN (20) | non A2/A24 | estrogen receptor-related protein |
|---|---|---|
| LCVKAMILL (21) | non A2/A24 | estrogen receptor 2 (ER beta) variant |
| MNQKLSPFM (22) | non A2/A24 | estrogen sulfotransferase |
| RYKKLKVE (23) | non A2/A24 | estrogen-related receptor beta |
| SKAKSLTDPS (24) | non A2/A24 | estrogen receptor binding protein variant |
| WFGIKAPE (25) | non 42/A24 | estrogen receptor binding protein variant |

Any of these polypeptides individually or in combination may be used as ESR1 polypeptides in the vaccine described herein.

The vaccine may include a vaccine vector. The vaccine vector may be a bacterial, yeast, viral or liposomal vaccine vector. The vaccine may be a DNA vaccine as well and not include a vaccine vector. The vaccine vector may be an adenovirus, adeno-associated virus, fowlpox, vaccinia, viral equine encephalitis virus, venezuelan equine encephalitis virus or other viral vaccine vectors. One method for generating adenovirus vectors is provided in Luo et al., Nature Protocols, (2007) 2: 1236-1247, which is incorporated herein by reference. The vaccine vector may contain the ESR1 polynucleotide or portions thereof. The vaccine vector may contain the ESR1 polypeptide or portions thereof. The vaccine vector may express the ESR1 polypeptide or portions thereof. ESR1 polypeptide or portions thereof may be expressed on the surface or interior of the vaccine vector. ESR1 polynucleotide or portions thereof may be carried within the vaccine vector and the ESR1 polypeptide or portions thereof may be expressed only after vaccination. ESR1 polypeptides or portions thereof may be expressed as a fusion protein or in conjunction with adjuvants or other immunostimulatory molecules to further enhance the immune response to the polypeptide.

Methods of treating a cancer or precancer, or of reducing the likelihood of the cancer or precancer developing resistance to a cancer therapeutic or prevention agent, are also provided. The methods include administering the vaccine as described above to a subject having cancer or precancer. The subject may be any mammal, suitably a human, domesticated animal such as a dog or cat, or a mouse or rat. A cancer therapeutic or prevention agent may be administered concurrently with, before or after administration of the vaccine.

The cancer therapeutic or prevention agents may be any agent capable of treating the cancer or inhibiting growth of cancer cells. Suitable agents include those which target HER2, HER1/EGFR, HER3, estrogen receptor or IGF1R. The therapeutic agent may be trastuzumab, lapatinib, pertuzumab or another HER2 or estrogen receptor targeting therapeutic agent or it may be an EGFR targeting therapeutic agent such as cetuximab or erlotanib, or it may be an anti-estrogen, or an agent that prevents estrogen synthesis such as an aromatase inhibitor. We have previously demonstrated that a HER3 vaccine can treat a HER2 positive cancer when used in combination with a therapeutic agent targeting HER2. An ESR1 vaccine should work similarly and the mutations provide unique sites for vaccination to differentiate cancer or precancer cells from normal cells. Cancer cells often develop resistance to therapeutic agents. Addition of vaccination with an ESR1 vaccine or passively transferred polyclonal antibodies specific for ESR1 will result in blocking resistance, inhibit cancer cell growth and result in treatment of the cancer.

Suitably the vaccinated subject develops an immune response to the mutated form of ESR1 in response to administration of the vaccine. The immune response may be an antibody or T cell immune response. For example the immune response may include antibody-dependent cellular cytotoxicity, polyclonal antibody response, complement dependent cellular cytotoxicity, cellular cytotoxicity, disruption of ligand binding, disruption of dimerization, mimicking ligand binding causing internalization of ESR1, or degradation of ESR1. The immune response may comprise an antibody response directed to at least a portion of ESR1, suitably a portion including the mutations. The immune response may be specific for a T cell or B cell epitope flanking or encompassing the mutations in SEQ ID NO: 1-3 or 5 or regions flanking the mutations in ESR1.

Reduction of the development of resistance can be measured in several ways. The resistance of the vaccinated subject may be compared to a similar subject that was not vaccinated as in the Examples. Alternatively, the reduction may be measured based on statistics generated regarding the likelihood of an individual being treated with the therapeutic agent to develop resistance versus that of individuals treated with the therapeutic agent and vaccinated with ESR1. The reduction in the likelihood of resistance of the cancer may also be measured by measuring the level of ESR1 expression on the surface of cancer cells. ESR1 expression is reduced on cancer cells after effective administration of the vaccine. The effectiveness of the vaccine in treating the cancer or reducing the likelihood of resistance can be measured by tracking the growth of the tumor or the growth rate of the tumor or cancer cells. A decrease in tumor size or in the rate of tumor growth is indicative of treatment of the cancer.

The cancer may be selected from any cancer capable of developing resistance to a therapeutic agent by increasing expression or activation of a protein by the cancer cells. In particular the cancer may be any cancer capable of developing resistance to a therapeutic agent which targets a HER family tyrosine kinase, suitably HER2, HER3, or EGFR or the estrogen receptor, suitably anti-estrogens. The cancer may develop resistance by increasing the expression of ESR1, mutating ESR1 or deleting a portion of ESR1 to avoid susceptibility to the therapeutic agent. Suitably the cancers are selected from breast, prostate, lung, ovarian, colon, rectal, pancreas, bladder, head and neck or liver cancers or precancers. The resistance may be due to a single or multiple changes, and the vaccine can target one or more of these changes, and/or include multiple antigens likely found in resistance cells, but not necessarily in all resistance cells.

Treating cancer includes, but is not limited to, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

Co-administration, or administration of more than one composition (i.e. a vaccine and a therapeutic agent) to a subject, indicates that the compositions may be administered in any order, at the same time or as part of a unitary composition. The two compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An effective amount or a therapeutically effective amount as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e. the vaccines and the therapeutic agents or checkpoint inhibitory agents) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal absorption. Thus the compositions may be formulated as an ingestable, injectable, topical or suppository formulation. The compositions may also be delivered with in a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce the growth of the cancer at least 10%, 20%, 30%, 40%, 50%, 60%, 70%, 80%, 90%, 100% or more as compared to no treatment or treatment with only the therapeutic agent. It is specifically contemplated that pharmaceutical preparations and compositions may palliate, block further growth or alleviate symptoms associated with the cancer without providing a cure, or, in some embodiments, may be used to cure the cancer and rid the subject of the disease.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The vaccine vector may be administered one time or more than one time to the subject to effectively boost the immune response against ESR1. If the vaccine is provided as a vaccine vector, the vaccine vector may be administered based on the number of particles delivered to the subject (i.e. plaque forming units or colony forming units). The subject may be administered $10^{12}$, $10^{11}$, $10^{10}$, $10^9$, $10^8$, $10^7$ or $10^6$ particles.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Materials and Methods

Viral Vectors: Mutations in the ESR1 plasmid were generated by site-directed mutatgenesis of a pENTR221-ESR1 plasmid obtained from the Orfeome (Dharmacon) to create ESR1 mutants Y537N, Y537S, D538G, and K303R. See SEQ ID Nos: 1-3 and 5, respectively. These genes were cloned into adenoviral vectors, which were then generated as previously described[1]. These genes were also cloned into lentiviral vectors (LX301 from Addgene) and used to generated cell lines with stable expression of these genes as previously described[2].

Cell Lines: Breast epithelial cell lines MM3MG, NMuMG, and MCF-7 were obtained from the American Tissue Culture Collection (ATCC), and were maintained according to ATCC recommendations. These lines were tested for *Mycoplasma* and DNA fingerprinted at the Duke Cell Culture Facility.

In Vitro Assays: Proliferation of stable cells was determined by MTT assay using 5,000 cells/well over the course of 3 days (against control counterparts) in 96-well plates. MTT growth assessments were done using a Bio-Rad plate reader after cell solubilization in DMSO. Soft agar assays for stable expression were done as described[2]. Briefly, 50,000 cells/well were plated in 0.3% soft agar (on a base of 0.6% soft agar) and allowed to grow for a period of 2 wk in DMEM with 10% FBS. At the end of this time, colonies of >15 cells were counted and scored. In experiments using inducible expression systems, Dox was added to the media at a concentration of 2 µg/ml (replaced weekly). Wound Scratch Assays were performed using p1000 tips, washing wounded plates with PBS (2×) and applying media before staining with Crystal Violet at 16 hours post-wounding. Pictures were taken using an Olympus IX73 using a 10× magnification objective. Luciferase Assays were performed by co-transfecting an luciferase reporter plasmids (SABiosciences) along with a CAG-LacZ control (Addgene) into modified 293T cells in estrogen-free conditions (phenol-red free media with charcoal stripped FBS) and assessing pathways signaling at 24 or 48 hpt using standard techniques with Luminometer (GloMax 96-well, Promega, Madison Wis.).

Animal Experiments: Experiments using BALB/c and SCID-Beige mice (obtained from Jackson Labs) were done in accordance with Duke Institutional Animal Care and Use Committee-approved protocols. For tumor vaccine experiments, BALB/c mice (Jackson Labs) were implanted with MM3MG modified cellsR2d16 tumors and genotyped by PCR as previously described[4]. In immune competent (BALB/c) and immuno-deficient animals (SCID-beige), stable cells were injected s.c. into the flank of SCID-beige mice (at indicated cells/animal) and measured as indicated. Tumor measurements were made using calipers and volumes calculated using the formula [v=width×width×(length/2)] whereas statistical differences were calculated using a mixed effects regression model using autoregressive covariance.

ELISPOT and ELISA Assays: Immunogenicity experiments involved footpad injection of Ad-ESR-WT, ESR1-mutant, and Ad-GFP vectors ($2.6 \times 10^{10}$ particles/mouse) in BALB/c animals. Fourteen days post-injection, mice were euthanized and splenocytes and sera were collected for analysis. IFN-γ ELISPOT assays (Mabtech Inc.) were done according to the manufacturer's instructions using overlapping ESR1 peptide mixes (2.6 μg/mL; BD Biosciences) as stimulating antigens and HIV-irrelevant overlapping peptide mixes as negative controls (BD Biosciences). Phorbol 12-myristate 13-acetate (50 ng/mL) and ionomycin (1 μg/mL) served as a positive control for splenocyte responsiveness. Antibodies were assessed using a sandwich-based ELISA method using ESR1 protein (10 ug/ml, Thermo-Fisher) as previously described using LacZ[5].

Figure 2:
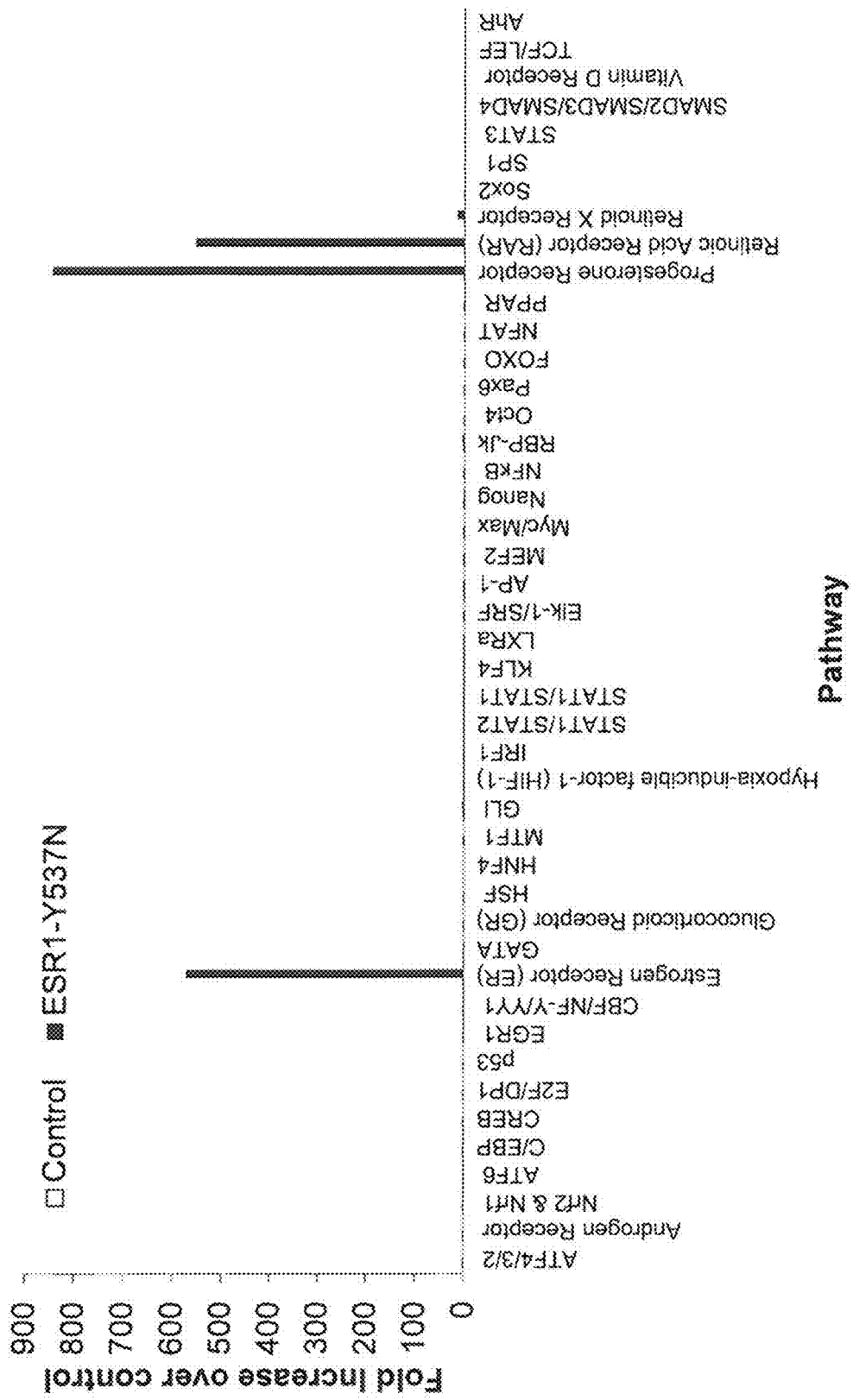
FIG. 2 is a graph showing analysis of ESR1-Y537N mutant signaling. 293T cells stably expressing the indicated genes were reverse transfected with 45 different pathway reporter luciferase vectors (180 ng/well), along with a LacZ control (20 ng) and plated in 96 well plates (20,000 cells per well). At 24 hours post-transfection, cells were lysed and luciferase activity measured (normalized to LacZ transfection control). N=4 per group.
Figure 3:
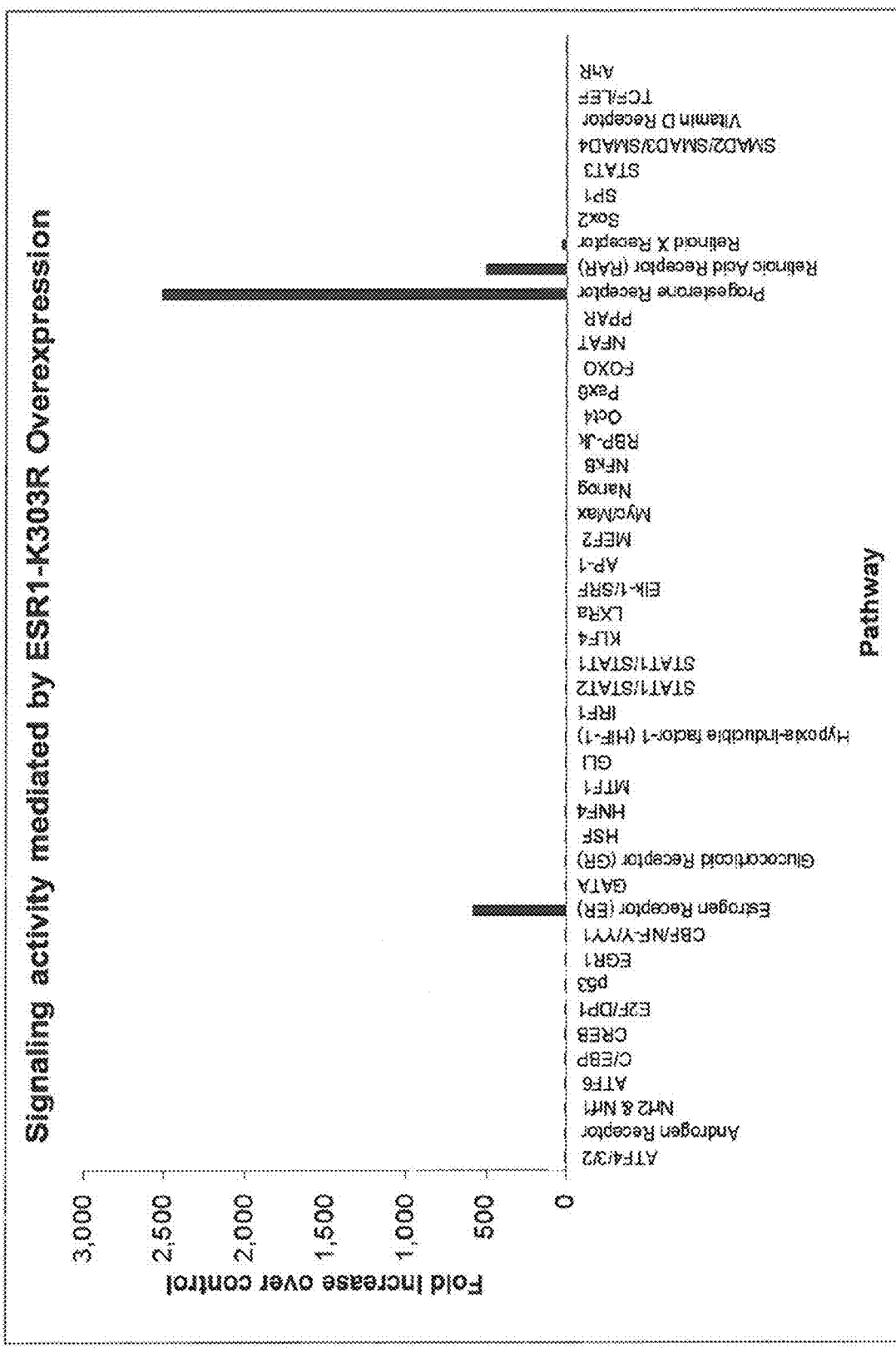
FIG. 3 is a graph showing analysis of ESR1-K303R mutant signaling. 293T cells stably expressing the indicated genes were reverse transfected with 45 different pathway reporter luciferase vectors (180 ng/well), along with a LacZ control (20 ng) and plated in 96 well plates (20,000 cells per well). At 24 hours post-transfection, cells were lysed and luciferase activity measured (normalized to LacZ transfection control). N=4 per group.
Figure 4:
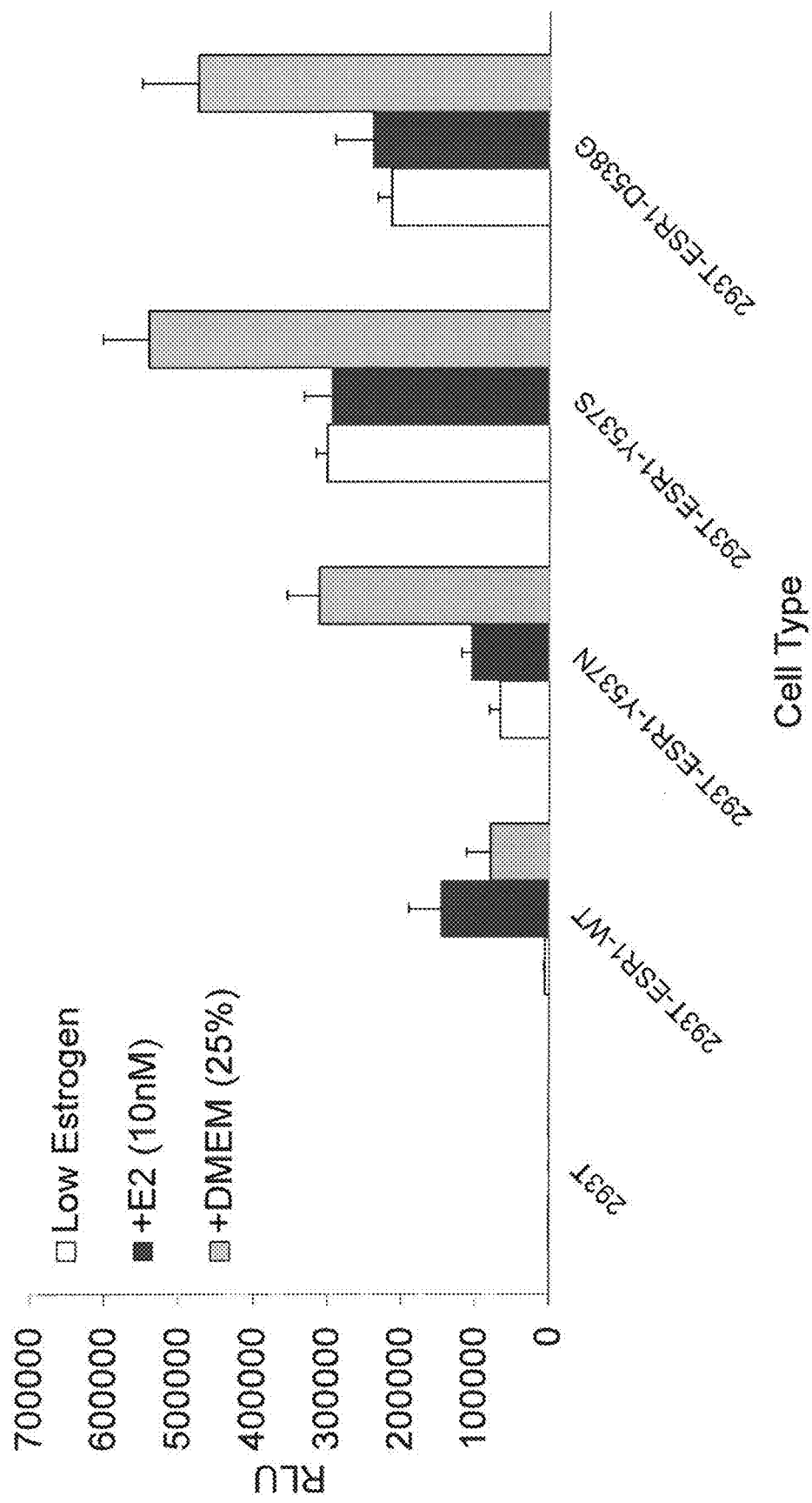
FIG. 4 is a graph showing ESR1 PR signaling with different mutants. 293T cells stably expressing the indicated genes were transfected with an PR luciferase reporter (180 ng), along with a LacZ control (20 ng) and plated in 96 well plates (20,000 cells per well). At 24 hours post-transfection, cells were lysed and luciferase activity measured (normalized to LacZ transfection control). N=4 per group.
Figure 5:
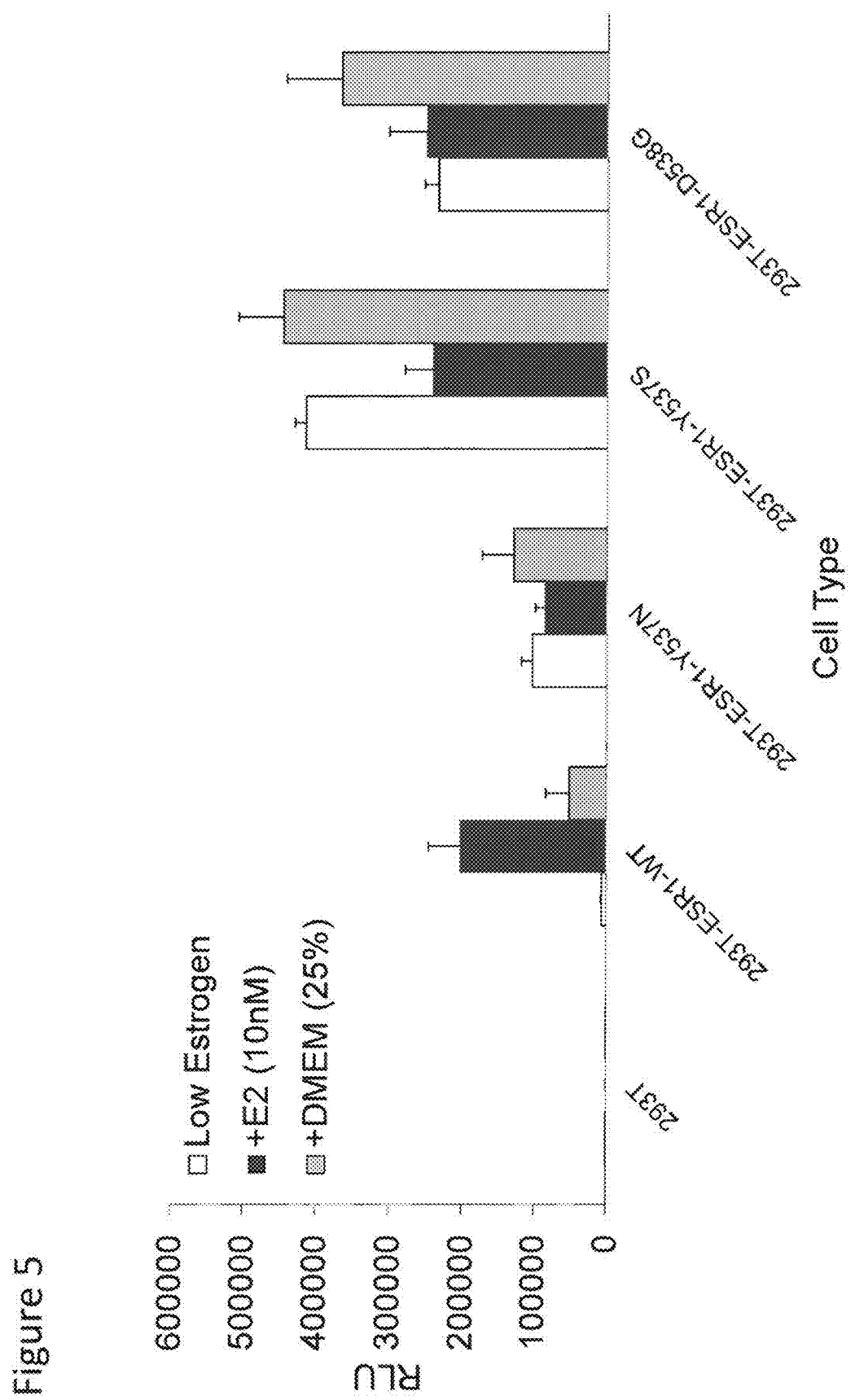
FIG. 5 is a graph showing ESR1 RAR signaling with different mutants. 293T cells stably expressing the indicated genes were transfected with an RAR luciferase reporter (180 ng), along with a LacZ control (20 ng) and plated in 96 well plates (20,000 cells per well). At 24 hours post-transfection, cells were lysed and luciferase activity measured (normalized to LacZ transfection control). N=4 per group.

Results:

To initially validate the importance of the identified ESR1 mutations, we first investigated their ability to elicit canonical estrogen-dependent signaling in the absence of exogenous estrogen stimulation. To test differences in ESR1 estrogen-dependent signaling, we generated 293T cells (which do not express detectable levels of ESR1) expressing ESR-WT, Y537N, Y537S, D538G, and K303R. Using a highly sensitive canonical ERE-pathway luciferase-based signaling reporter system, we then determined how estrogen-free and estrogen-induced ERE pathways were affected by ESR L-WT or mutant expression. We found that ERE signaling was strongly activated in ESR1-WT expressing cells when stimulated with estrogen in comparison to ESR1-WT expressing non-stimulated cells or control cells stimulated with estrogen (FIG. 1). More importantly, all mutant forms of ESR1 strongly induced the ERE pathway in the absence of estrogen (FIG. 1). To get a broader view of potential pathways affected by these mutants, we utilized a high throughput 45-pathways reporter array (SABiosciences) for both estrogen receptor mutation classes (represented by ESR1-Y537S and K303R). These experiments revealed that both classes of estrogen receptor mutants elicited ERE signaling, but also PR and RAR signaling pathways (FIGS. 2 and 3). Having identified the three critical pathways activated by estrogen receptor mutants, we then validated their activity in ESR1-WT expressing cells stimulated with estrogen, as well as in the other ligand-binding domain mutants (ESR1-Y537N and ESR1-D538G) (FIG. 4-5). Our results demonstrate that these pathways are stimulated by ESR1-WT only in the presence of estrogen, but are constitutively active in mutant ESR1 expressing lines in the absence of estrogen stimulation.

Having demonstrated that these mutants can confer robust ESR1 canonical signaling that mimics estrogen stimulation, we next wanted to see if these receptors could compensate for loss of estrogen stimulation in ER+ breast cancer. To test this, we constructed a series of MCF-7 cells with expression of wild-type or mutated ESR1 and implanted these cells into male mice (low estrogen levels) without any exogenous estrogen stimulation. As a control, we implanted both MCF-7 control cells (high ESR1) and MCF-7-ESR1-Y537N cells into female mice supplemented with exogenous estrogen. As predicted exogenous estrogen supplementation allowed for 100% tumor growth, while estrogen starvation resulted in strongly reduced tumor growth of control cells in 13% of mice and no control tumor growth in 87% of mice. This was in direct contrast to ESR1 mutant expressing cells which formed tumors in 80-100% of mice without exogenous estrogen supplementation (FIG. 6). However, ESR1-Y537N tumor growth in low estrogen conditions was somewhat slower non-supplemented mice, thus potentially demonstrating an effect from ESR1-WT present in MCF-7 cells. Collectively, these results demonstrate that these identified ESR1 mutants can compensate for suppression of estrogen in ER+ breast cancer in vivo, suggesting their efficacy as anti-estrogen therapies resistance mechanisms.

Figure 7:
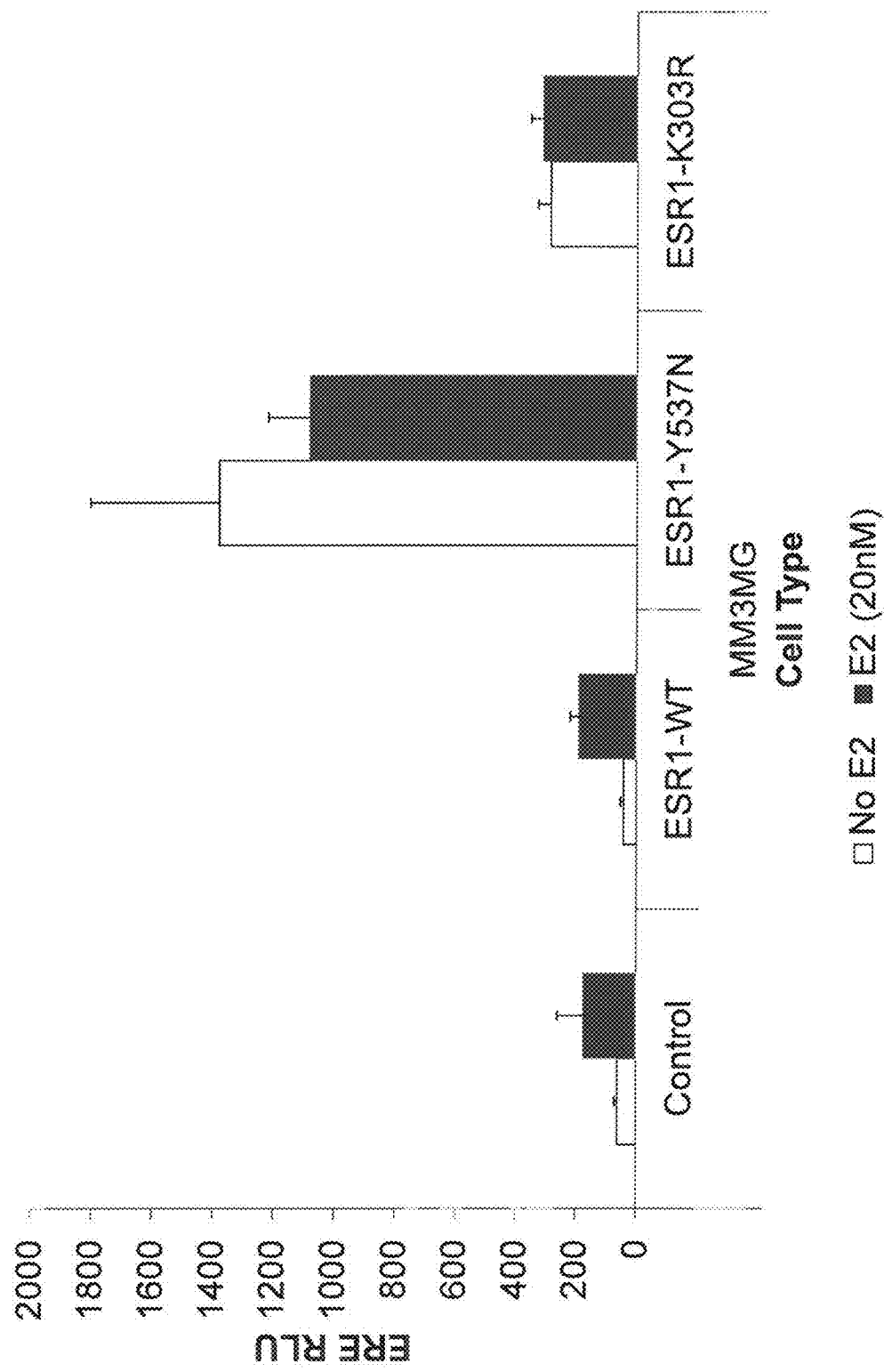
FIG. 7 is a graph showing ESR1 ERE signaling in murine mammary cells with different mutants. MM3MG cells stably expressing the indicated genes were transfected with an ERE luciferase reporter (180 ng), along with a LacZ control (20 ng) using FugeneHD. At 24 hours post-transfection, cells were split and plated into 96 well plates (20,000 cells per well) where they were treated with or without 17B-Estradiol (20 nM) as indicated. 24 hours post-treatment, cells were lysed and luciferase activity measured (normalized to LacZ transfection control). N=4 per group.
Figure 8:
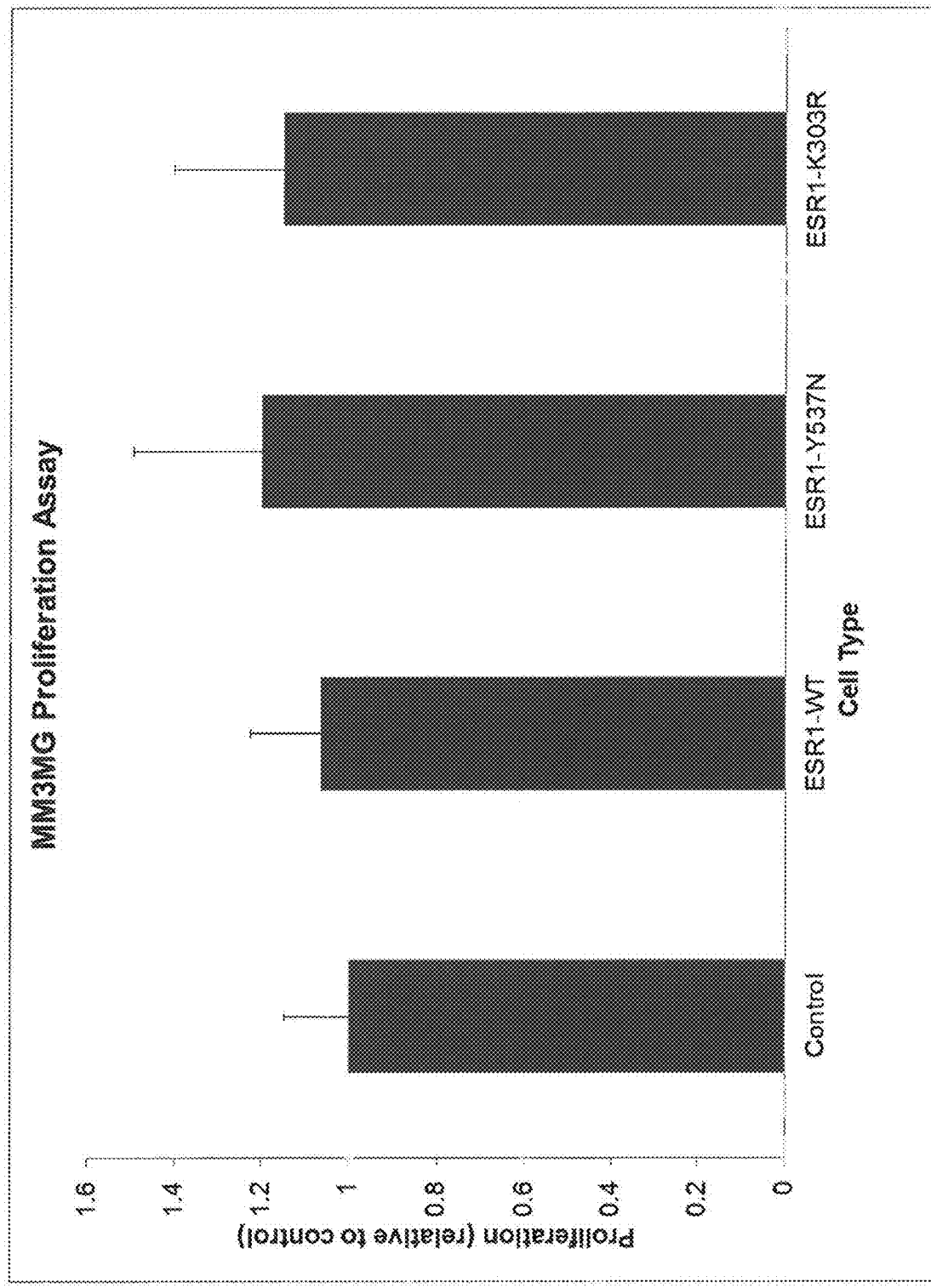
FIG. 8 is a graph showing that ESR1 mutants in murine mammary cells do not confer proliferative advantage. MM3MG cells stably expressing the indicated genes were plated in 96-well plates (5,000 per well) and assessed at 4 days post-plating by MTT Assay (N=12, bars indicate SD).
Figure 10:
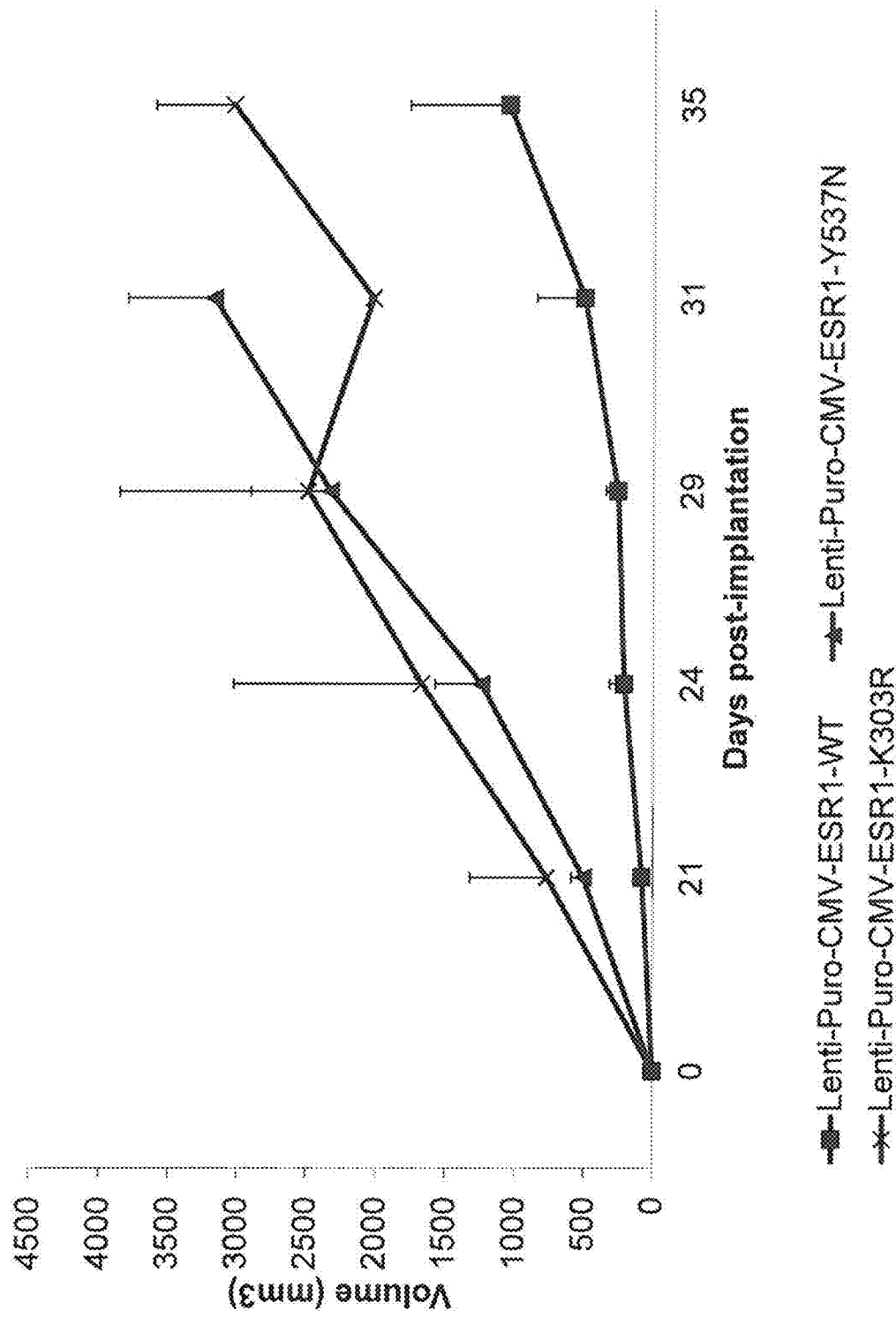
FIG. 10 is a graph showing ESR1 mutants in murine mammary cells can confer a proliferative advantage in vivo. MM3MG cells stably expressing the indicated genes were implanted subcutaneously into SCID-Beige mice (100,000 per mouse in PBS) at days 0. Tumor growth was measured by calipers at the indicated days (N=5, bars represent SE).

To determine if we could successfully immunologically target these mutated versions of ESR1 in a breast cancer setting, we first needed to establish a mouse model system of ER+ breast cancer. This model system would ideally have some form of transformation driven estrogen dependence whereby estrogen signaling was driven by these mutant versions of ESR1. To establish this model system, we first transduced MM3MG mammary breast epithelial cells with lentiviral vectors to stably express the various forms of ESR1. This mammary epithelial line was only weakly transformed (data not shown), expressed low endogenous levels of ESR1, and from a BALB/c background which would allow for immune studies to be performed in syngeneic BALB/c mice. After establishing these cell lines for each class of ESR1 mutant with a wild-type ESR1 control, we first confirmed that ERE signaling occurred in control lines after estrogen stimulation and in an ESR1 mutant line without estrogen stimulation (FIG. 7). To determine if these mutants had oncogenic capacity in these cells, we ascertained proliferation, anchorage-independent growth in soft agar, as well tumor formation and growth in vivo. Using MTT-based assays, we found that these mutants had no effect on proliferation (FIG. 8), although we did observe a significant increase in anchorage-independent growth when ESR1-Y537N was expressed in soft agar assays (FIG. 9). Finally, we injected ESR1-WT, ESR1-K303R, and ESR1-Y537N to determine the effect of ESR1-WT or mutated ESR1 on tumor growth in vivo. Notably, we found that both mutant ESR1 expressing lines grew more rapidly in these mice, demonstrating an oncogenic capacity of mutant estrogen signaling in these cells. Collectively, these results demonstrate that these mutants can confer estrogen-independent canonical signaling through several different pathways and that these mutant ESR1 can enhance murine mammary cell tumor growth in vivo.

Figure 11:
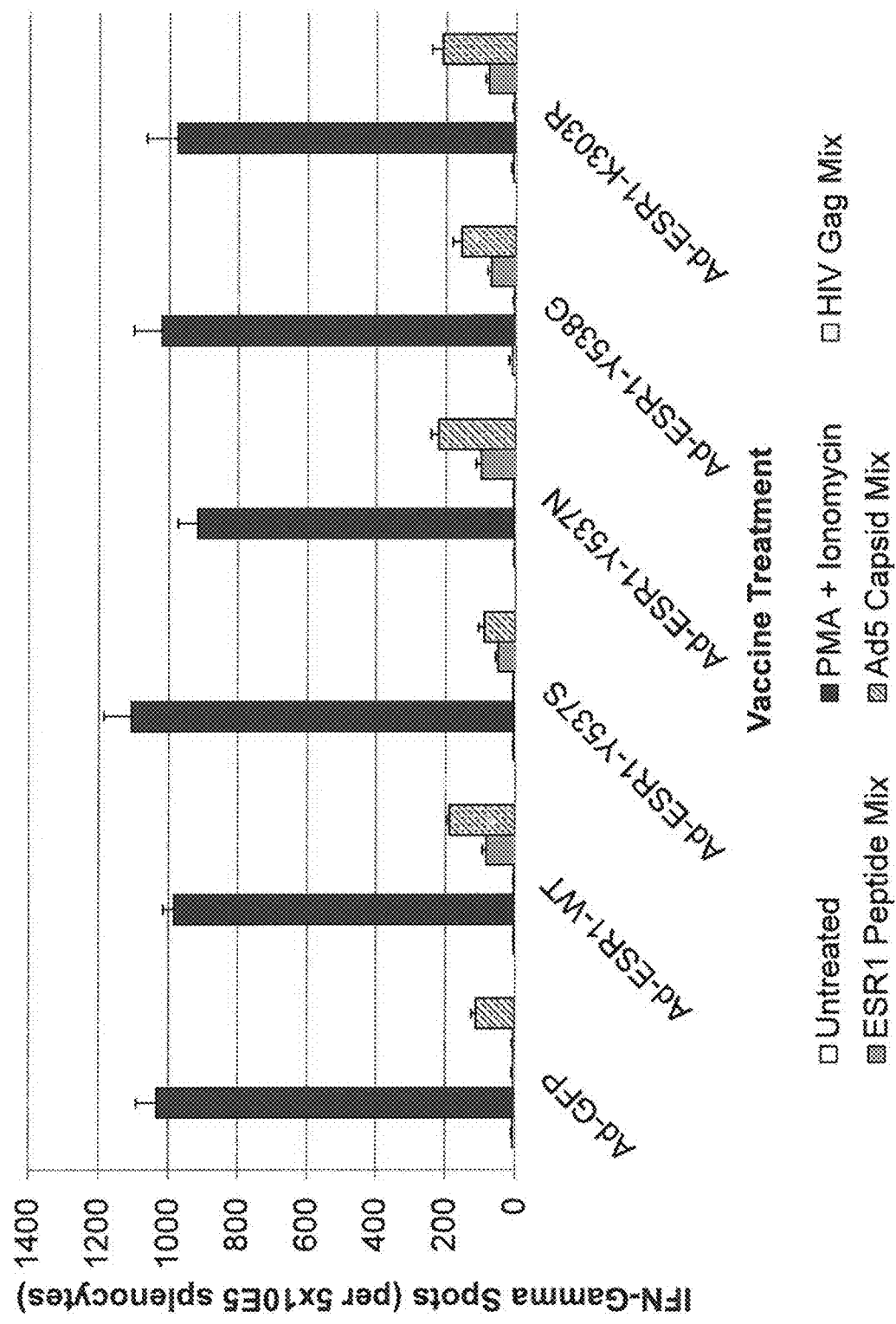
FIG. 11 is a graph showing that the adenoviral vaccines targeting ESR1 elicit significant T-cell responses against ESR1-specific epitopes. C57 mice were vaccinated using the indicated adenoviral vectors (2.6E10 viral particles per mouse via footpad) and sacrificed at 2 wpi. ELISPOT assays were then performed using 500 k splenocytes per well against the indicated antigen stimuli (N=5, bars represent SD).
Figure 12:
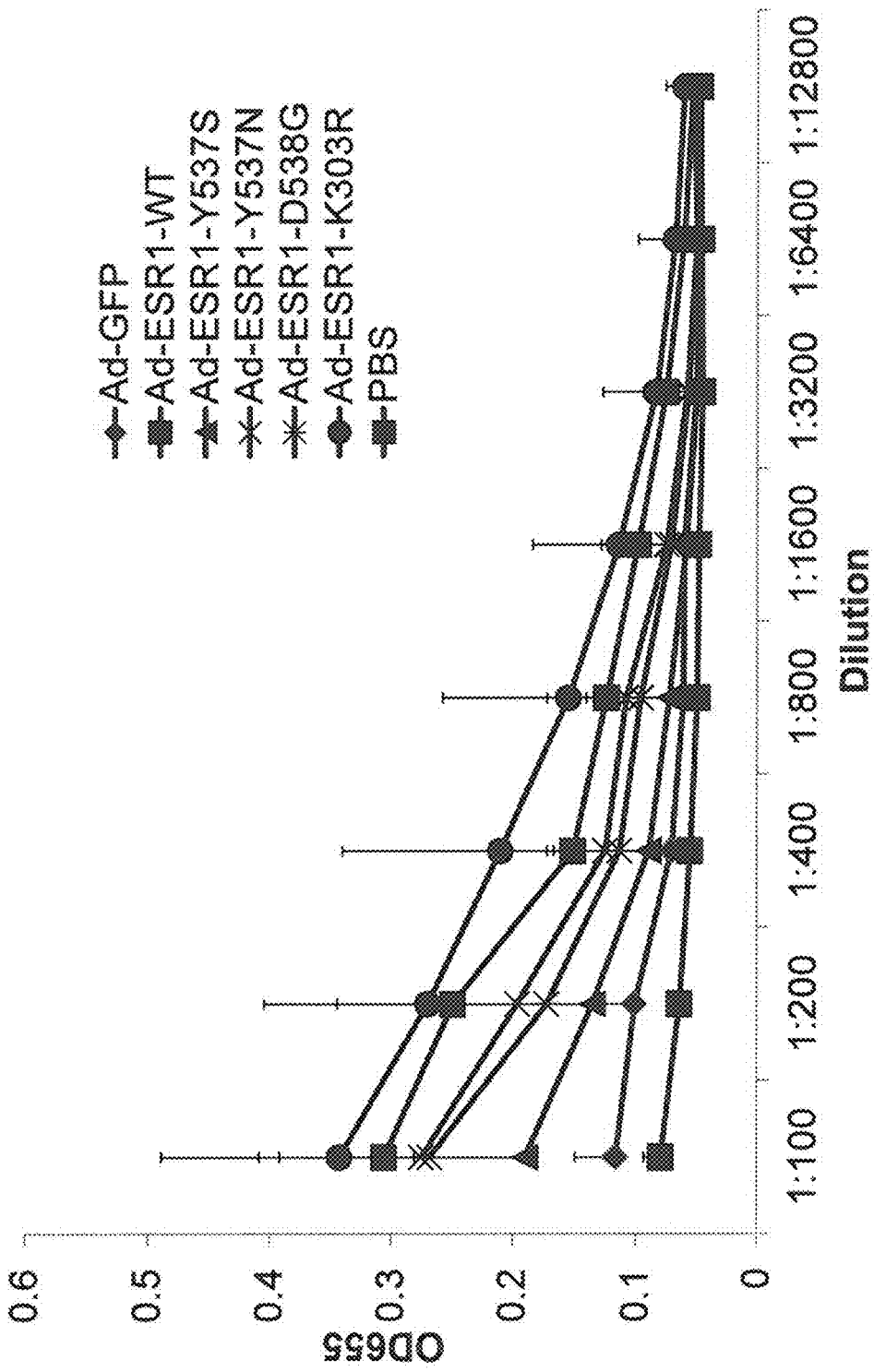
FIG. 12 is a graph showing that the adenoviral vaccines targeting ESR1 elicit significant B-cell responses against ESR1-specific epitopes. C57 mice were vaccinated using the indicated adenoviral vectors (2.6E10 viral particles per mouse via footpad) and sacrificed at 2 wpi. ELISA assays were then performed using ESR1 coated plates (Thermo Fisher, 10 µg/ml) and using an anti-mouse IgG-HRP secondary antibody (CST, 1:1000 dilution) to detect ESR1-specific IgG antibodies. (N=5, bars represent SD).

Recent clinical studies have indicated that ESR1 mutations can be responsible for tamoxifen resistance in patients, which is supported by our findings using ESR1 mutant expressing cell lines. We hypothesized that immunologic targeting of these genes may prevent the development of resistance and potentially be a therapy for ER+ breast cancer. As such, we wished to explore the capacity of a vaccine targeting these oncogenic mutant forms of ESR1 to elicit anti-tumor responses. As a preliminary step, we took advantage of our adenoviral vector platform, which we had previously demonstrated to be capable of eliciting strong anti-tumor immunity against multiple Tumor Associated Antigens, including HER2. Using this platform, we constructed adenoviral vectors encoding wild-type and mutant forms of ESR1. After constructing and purifying these vectors, we ascertained their ability to elicit ESR1-specific immunity in BALB/c mice. Using a ESR1-specific ELISPOT assay, we determined that vaccination with ESR1 or mutant ESR1 genes strongly elicited significant T-cell mediated immunity to ESR-specific epitopes (FIG. 11), while a ESR1-specific ELISA assay demonstrated significant ESR1 specific antibody responses (FIG. 12).

Figure 13:
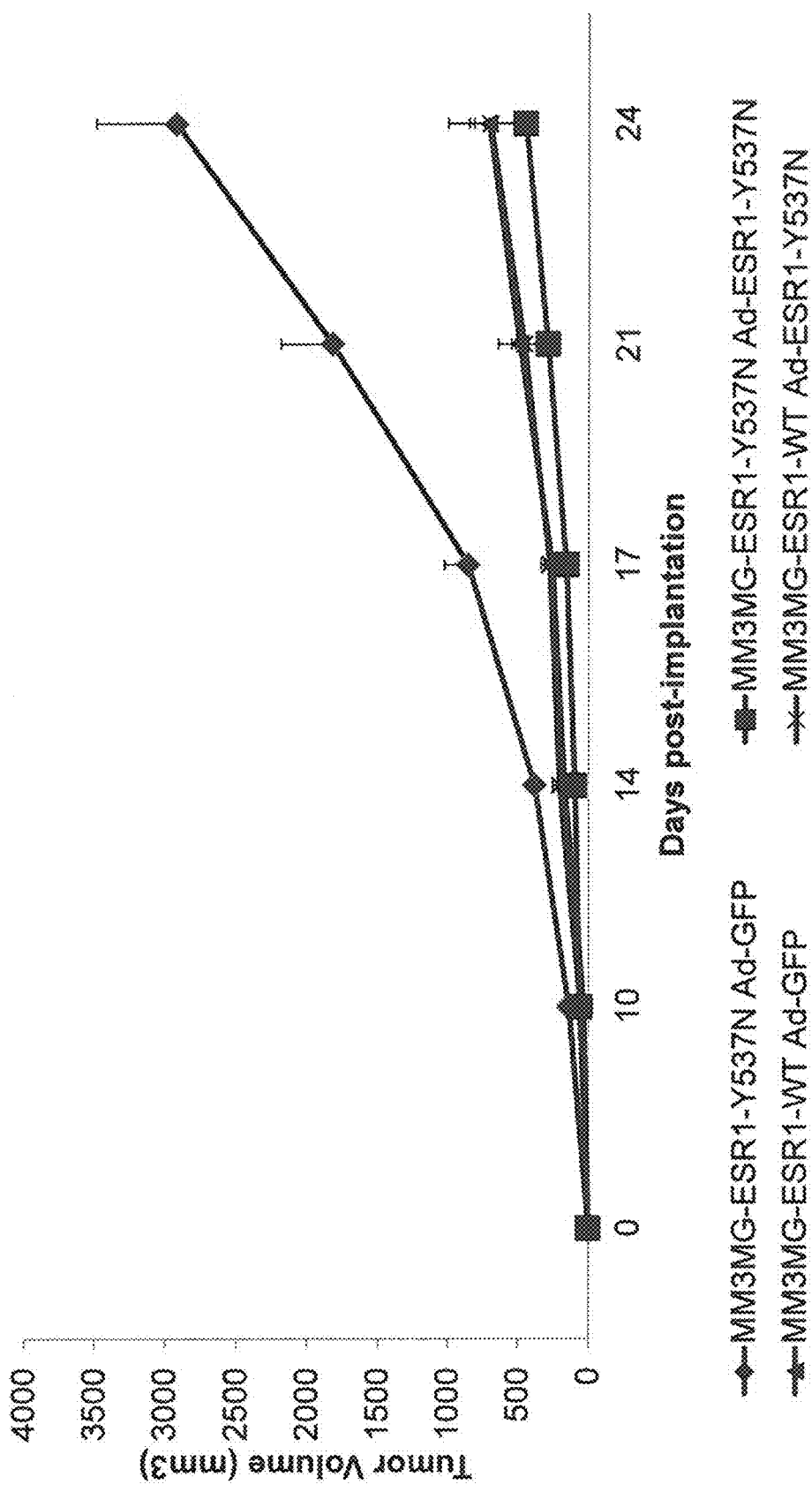
FIG. 13 is a graph showing that targeted vaccination against ESR1 mutants suppresses the growth of ESR1-mutant expressing cells. BALB/c mice were vaccinated using the indicated adenoviral vectors (2.6E10 viral particles per mouse via footpad) and MM3MG cells stably expressing the indicated genes were implanted at 2 wpi (100,000 per mouse in PBS, indicated at day 0). Tumor growth was measured by calipers at the indicated days (N=5, bars represent SE).

Having thus demonstrated these vaccines were capable of eliciting B-cell and T-cell ESR1-specific immunity, we next sought to determine if vaccination against a constitutively active oncogenic ESR1 mutant could significantly retard tumor growth. Having developed ESR1-mut transformed breast cancer lines capable of growing in immunocompetent transgenic animals, we next implanted these cells or ESR1-WT expressing counterparts into animals and tested if anti-ESR1 responses elicited by a preventative vaccination (2 weeks prior to injection) could retard ESR1-mediated growth. Our results demonstrated that an Ad-ESR1-Y537N vaccine formulation could significantly suppress ESR1-Y537N mediated tumor growth, but surprisingly did not affect MM3MG-ESR1-WT tumor growth (FIG. 13).

Figure 14:
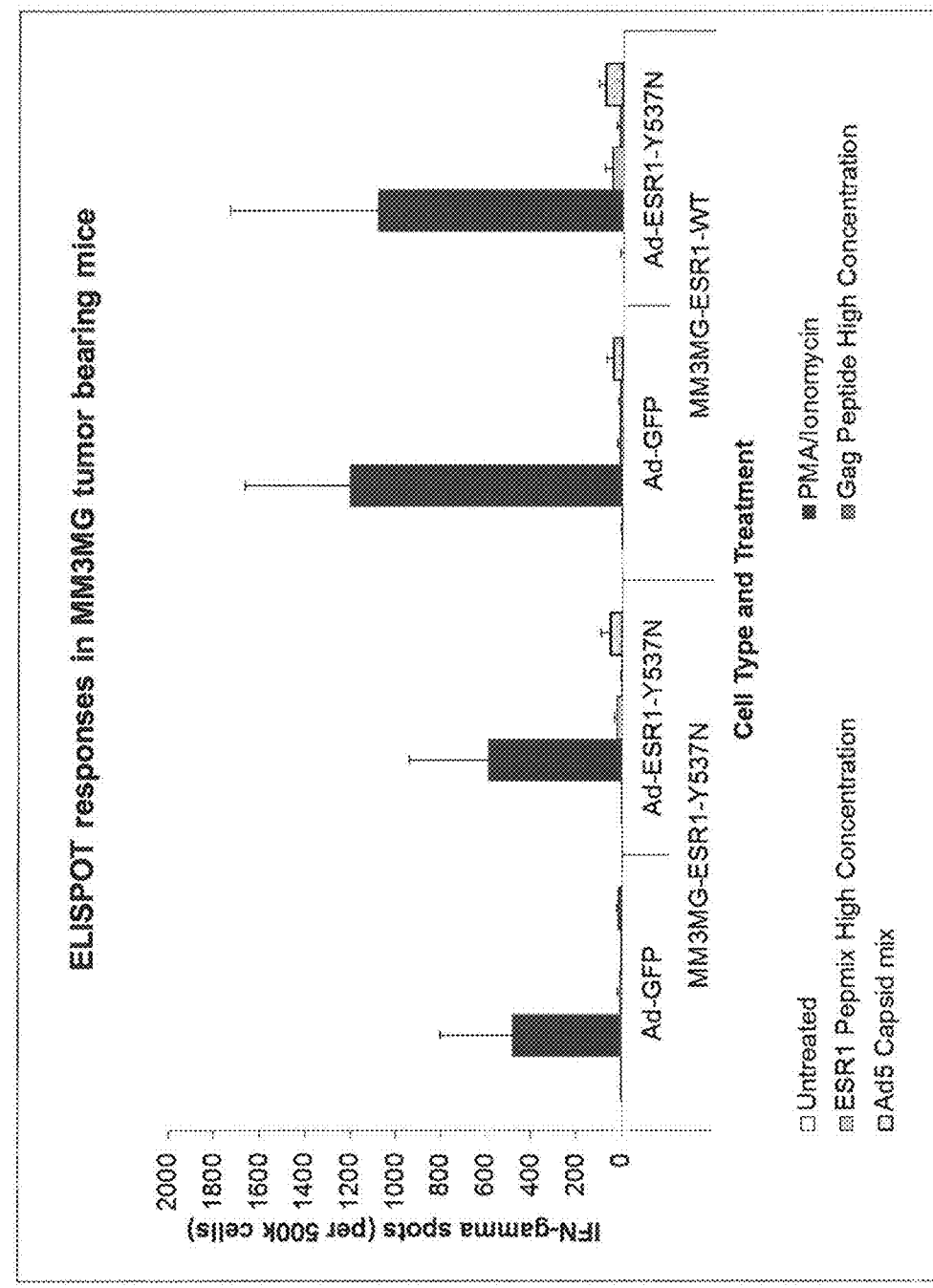
FIG. 14 is a graph showing that the adenoviral vaccines targeting ESR1 elicit T-cell responses against ESR1-specific epitopes in tumor-bearing mice. BALB/c mice were vaccinated using the indicated adenoviral vectors (2.6E10 viral particles per mouse via footpad) and MM3MG cells stably expressing the indicated genes were implanted at 2 wpi (100,000 per mouse in PBS, indicated at day 0). Tumor growth was measured by calipers at the indicated days (N=5, bars represent SE). ELISPOT assays were then performed using 500 k splenocytes per well against the indicated antigen stimuli (N=5, bars represent SD).

Additionally, we found that after a control Ad-GFP vaccination, MM3MG-ESR1-Y537N cells grew much more rapidly than MM3MG-ESR1-WT cells, thus demonstrating that an active form of ESR1 also enhanced growth in an immunocompetent setting. This was confirmed by ELISPOT assays that indicated Ad-ESR1-Y537N could elicit ESR1-specific T-cell responses in vaccinated tumor-bearing animals (FIG. 14). These results suggest that therapies targeting ESR1 mutants can have a significant immunologic impact on tumor growth in cancers driven by specific oncogenic mutations. As such, we expect that the use of checkpoint inhibitors in combination with our vaccine will allow for significant and sustained immune responses to critical oncogenic drivers and may prevent the development of resistance mediated by ESR1 mutation.

1. Hartman, Z. C. et al. An adenoviral vaccine encoding full-length inactivated human Her2 exhibits potent immunogenicty and enhanced therapeutic efficacy without oncogenicity. *Clin. Cancer Res.* 16, 1466-1477 (2010).
2. Hartman, Z. C. et al. Growth of triple-negative breast cancer cells relies upon coordinate autocrine expression of the proinflammatory cytokines IL-6 and IL-8. *Cancer Res* 73, 3470-80 (2013).
3. Hartman, Z. C. et al. HER2 overexpression elicits a proinflammatory IL-6 autocrine signaling loop that is critical for tumorigenesis. *Cancer Res.* 71, 4380-4391 (2011).
4. Kershaw, M. H. et al. Gene-engineered T cells as a superior adjuvant therapy for metastatic cancer 1. *J. Immumol.* 173, 2143-2150 (2004).
5. Hartman, Z. C. et al. Ligand-independent toll-like receptor signals generated by ectopic overexpression of MyD88 generate local and systemic antitumor immunity. *Cancer Res.* 70, 7209-7220 (2010).
6. Early Breast Cancer Trialists' Collaborative, G. et al. Relevance of breast cancer hormone receptors and other factors to the efficacy of adjuvant tamoxifen: patient-level meta-analysis of randomised trials. *Lancet* 378, 771-84 (2011).
7. Baum, M. et al. Anastrozole alone or in combination with tamoxifen versus tamoxifen alone for adjuvant treatment of postmenopausal women with early breast cancer: first results of the ATAC randomised trial. *Lancet* 359, 2131-9 (2002).
8. Nabholtz, J. M. et al. Anastrozole is superior to tamoxifen as first-line therapy for advanced breast cancer in postmenopausal women: results of a North American multicenter randomized trial. Arimidex Study Group. *J Clin Oncol* 18, 3758-67 (2000).
9. Ignatiadis, M. & Sotiriou, C. Luminal breast cancer: from biology to treatment. *Nat Rev Clin Oncol* 10, 494-506 (2013).
10. Yerushalmi, R. et al. Tumor markers in metastatic breast cancer subtypes: frequency of elevation and correlation with outcome. *Ann Oncol* 23, 338-45 (2012).
11. Yerushalmi, R. et al. Patterns of relapse in breast cancer changes over time. *Breast Cancer Res Treat* 120, 753-9 (2010).
12. Kennecke, H. et al. Metastatic behavior of breast cancer subtypes. *J Clin Oncol* 28, 3271-7(2010).

We claim:

1. A method of treating a cancer or precancer or of reducing the likelihood of the cancer developing resistance to a cancer therapeutic or prevention agent comprising administering a vaccine vector comprising a polynucleotide encoding an ESR1 polypeptide comprising SEQ ID NO: 2 or a peptide fragment of at least eight amino acids from SEQ ID NO:2 including the mutation at amino acid residue S537 to a subject having the cancer or precancer, wherein the cancer or precancer comprises a Y537S mutation in ESR1, and wherein administration of the vaccine vector to the subject treats the cancer or precancer, reduces the likelihood of the cancer or precancer developing resistance to the cancer therapeutic or prevention agent or reverses resistance of the cancer or precancer to the cancer therapeutic or prevention agent.

2. The method of claim 1, wherein the vaccine is administered concurrently with, before or after administration of the cancer therapeutic or prevention agent.

3. The method of claim 2, wherein the cancer therapeutic or prevention agent is an agent targeting HER2, HER1, estrogen receptor, or IGF1R.

4. The method of claim 1, wherein the vaccine is administered concurrently with, before or after administration of a checkpoint inhibitor immunomodulatory agent.

5. The method of claim 4, wherein the checkpoint inhibitor immunomodulatory agent is a CTLA-4 or PD1 antagonistic antibody.

6. The method of claim 1, wherein the cancer or precancer is selected from a breast, prostate, lung, ovarian, colon, rectal, pancreas, bladder, head and neck or liver cancer or precancer.

7. The method of claim 1, wherein the subject develops an immune response to ESR1.

8. The method of claim 7, wherein the immune response comprises an antibody response or a T cell mediated response.

9. The method of claim 7, wherein the immune response includes at least one of antibody-dependent cellular cytotoxicity, polyclonal antibody response, complement dependent cellular cytotoxicity, cellular cytotoxicity, disruption of ligand binding, disruption of dimerization, mimicking ligand binding causing internalization of ESR1, or degradation of ESR1.

10. The method of claim 7, wherein the immune response comprises an antibody response directed to at least a portion of SEQ ID NO: 2.

11. The method of claim 1, wherein administration of the vaccine results in a reduction of ESR1 expression on cancer or precancer cells after administration of the vaccine as compared to the level of ESR1 on the cells prior to vaccination.

12. The method of claim 1, wherein administration results in decreased tumor growth rate or decreased tumor size after administration as compared to prior to administration.

13. The method of claim 1, wherein the cancer therapeutic or prevention agent is selected from trastuzumab, lapatinib, cetuximab, pertuzumab and erlotinib.

14. The method of claim 1, wherein the ESR1 polypeptide consists of a polypeptide selected from the group consisting of SEQ ID NO:2 and a peptide fragment of at least eight amino acids from SEQ ID NO:2 including the mutation at amino acid residue S537.

15. The method of claim 1, wherein the vaccine vector further comprises a HER3 polypeptide, HER2 polypeptide, a mutant form of a HER3 polypeptide or a mutant form of a HER2 polypeptide.

16. The method of claim 1, wherein the vaccine vector is selected from the group consisting of adenovirus, adeno-associated virus (AAV), fowlpox, vaccinia virus, and Venezuelen equine encephalitis virus.

* * * * *